(12) United States Patent
Cummings et al.

(10) Patent No.: US 6,322,563 B1
(45) Date of Patent: Nov. 27, 2001

(54) SMALL TISSUE AND MEMBRANE FIXATION APPARATUS AND METHODS FOR USE THEREOF

(75) Inventors: Joel W. Cummings, Tyngsboro; Roland Deangelis, Milton; Brian Clark, Somerville, all of MA (US); David Schiff, Highland Park, NJ (US); Paul Mulhauser, New York, NY (US); Jesse Gala, Summit, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/397,832

(22) Filed: Sep. 17, 1999

(51) Int. Cl.[7] .................................................. A61B 17/84
(52) U.S. Cl. ............................................. 606/72; 606/104
(58) Field of Search ................................. 606/72–78, 151, 606/213, 104; 411/439, 500

(56) References Cited

U.S. PATENT DOCUMENTS

| | | |
|---|---|---|
| 4,532,926 | 8/1985 | O'Holla . |
| 4,846,835 | 7/1989 | Grande . |
| 4,873,976 | 10/1989 | Schreiber . |
| 4,895,148 | 1/1990 | Bays et al. . |
| 4,924,865 | 5/1990 | Bays et al. . |
| 4,976,715 | 12/1990 | Bays et al. . |
| 4,994,073 * | 2/1991 | Green .................................. 606/220 |
| 5,013,316 * | 5/1991 | Goble et al. ......................... 606/72 |
| 5,059,206 | 10/1991 | Winters . |
| 5,102,421 * | 4/1992 | Anspach, Jr. ....................... 606/232 |
| 5,129,906 | 7/1992 | Ross et al. . |
| 5,203,864 * | 4/1993 | Phillips .............................. 606/151 |
| 5,236,431 * | 8/1993 | Gogolewski et al. ................ 606/72 |
| 5,246,441 | 9/1993 | Ross et al. . |
| 5,376,097 | 12/1994 | Phillips . |
| 5,443,482 * | 8/1995 | Stone et al. ......................... 606/232 |
| 5,480,403 * | 1/1996 | Lee et al. ............................. 606/72 |
| 5,562,704 | 10/1996 | Tamminmaki et al. . |
| 5,569,264 | 10/1996 | Tamminmaki et al. . |
| 5,618,314 * | 4/1997 | Harwin et al. ...................... 606/232 |
| 5,636,442 | 6/1997 | Wain et al. . |
| 5,674,247 | 10/1997 | Sohn . |
| 5,723,008 * | 3/1998 | Gordon ............................... 623/13 |
| 5,723,331 | 3/1998 | Tubo et al. . |
| 5,725,541 * | 3/1998 | Anspach, III et al. ............. 606/151 |
| 5,815,924 | 10/1998 | Apprille, Jr. et al. . |
| 5,827,298 | 10/1998 | Hart et al. . |
| 5,843,084 | 12/1998 | Hart et al. . |
| 5,891,160 * | 4/1999 | Williamson, IV et al. .......... 606/144 |
| 5,941,439 | 8/1999 | Kammerer et al. . |
| 6,017,348 | 1/2000 | Hart et al. . |
| 6,132,434 * | 10/2000 | Sherman et al. ...................... 606/78 |

* cited by examiner

Primary Examiner—Jeffrey A. Smith
Assistant Examiner—Michael B. Priddy
(74) Attorney, Agent, or Firm—Richard D. Allison; Thomas J. DesRosier

(57) ABSTRACT

The present invention relates to new surgical fasteners and methods of using the surgical fasteners. The surgical fasteners of the invention are in the form of tacks and comprise generally an elongate rod, a sharp conical head, a tail, and a transverse locking member extending from the tail above the plane of the rod. The fasteners are inserted into a bodily cavity for tissue and membrane fixation and approximation by the use of tack applicators. The tack applicators of the invention generally comprise an elongate handle, a loading tip and a carrier assembly that is removably inserted into the loading tip. The tacks are inserted and locked into the carrier assembly from which they may be disengaged.

15 Claims, 28 Drawing Sheets

SMALL TISSUE AND MEMBRANE FIXATION APPARATUS AND METHODS FOR USE THEREOF

FIELD OF THE INVENTION

The present invention relates to surgical fastener systems, and more particularly to surgical fasteners in the form of tacks, and to apparatus and methods for application of surgical fasteners for approximation and fixation of tissue and membranes.

BACKGROUND OF THE INVENTION

During surgical procedures, tissue and membrane fixation and approximation are often necessary. Various types of surgical fastening devices are used for accomplishing such functions. Some conventional fastening devices include, for example, sutures, staples, screws, clips and anchoring devices.

Sutures are generally used in tissue approximation. However, sutures require significant skill for precise placement and, if multiple closures are required, are time consuming to apply. Additionally it is often not possible to use sutures to approximate tissue and membrane located inside many tight areas of the body. Staples generally are used to repair large areas and typically require minimal precision in their placement. Clips are typically used in endoscopic and laparoscopic closure or ligation of vessels.

Some fasteners having a generally tack-like structure have been developed. Said fasteners are disclosed in, for example, U.S. Pat. Nos. 4,873,976; 5,059,206; 5,246,441; 5,376,097; 5,562,704; 5,827,298; and 5,843,084.

Such tack-like structures generally comprise a shaft, a front portion and a back base portion. Additionally, each structure further comprises a type of barb-like or arresting means along the body to aid in holding the structure within the body. The focus of use of these tack-like structures is generally for repairing the meniscus. Thus, these tack-like structures are relatively large, with lengths ranging from about 0.2–0.64 inch and diameters ranging from about 0.04 to 0.07 inch. Further, they are designed to either have a significantly rigid shaft for insertion into the tough meniscal area or they are inserted while held within a penetrating tool having a sharp or pointed leading edge. In the situation where a penetrating tool is used, the tool cuts through the tissue and the tack-like fastener is carried through the tissue by the tool, and deposited in the tissue. This is disadvantageous in part because the tool which carries the tack must be larger than the tack. This leads to a larger cut within the tissue than necessary, and an increase in trauma to the area. Additionally, when the fasteners have barb means or arresting means protruding from the shaft, the tool must accordingly be made even larger to house the barb-like or arresting means. Alternatively, where the barb means or arresting means protrude outside of the tool or where no tool is used, the barb-like or arresting means make cuts in the tissue as the tack-like fastener is inserted, thereby increasing trauma to the area.

There is a need for surgical fastening devices that are quickly applied and are suitable for small tissue approximation in situations requiring multiple points of connection and fine precision. Due to the nature of such tissue repair, small and relatively flexible surgical fasteners are needed. For example, surgical repair of cartilage involves the affixation of a temporary covering, such as the periosteum, to a portion of cartilage. Small and flexible fasteners are required for the fixation of the delicate and thin covering to the generally thin underlying cartilage, and the fasteners must be inserted close to the edges of the covering without tearing through the edges of the covering. Accordingly, there is also a need for a method of handling small sized, flexible fasteners for proper alignment and insertion into the body. Additionally, there is a need for surgical fastening devices and methods that may be used to approximate tissue and membrane or other tissue located in tight areas inside of the body. Further needed are surgical fastening devices and methods of inserting the surgical fasteners to minimize trauma to the area during insertion.

SUMMARY OF THE INVENTION

The present invention provides novel surgical fasteners and apparatus and methods for use thereof.

The surgical fastener of the present invention is generally in the form of a tack, and comprises a conical head, a tail section, and an elongate, preferably flexible, rod extending in between the conical head and the tail. The elongate rod and the conical head lie generally along the same longitudinal axis, and the elongate rod has a diameter less than the proximal diameter of the conical head. Thus, the back (proximal) surface of the conical head extends beyond and is preferably generally normal, or perpendicular to, the outer surface of the elongate rod. The tail extends radially from a proximal portion of the rod. Extending from the tail is a transverse locking member that is offset from the longitudinal axis of the head and the rod.

In preferred embodiments, the distal portion of the tail section forms an acute angle with a back portion of the rod, and the transverse locking member is generally formed by a pair of cylindrical or frusto-cylindrical protrusions located on each side of the tail section, offset from the axis of the head and rod members.

The preferred location of the transverse locking member, offset from the longitudinal axis of the head and the rod, aids in the positioning and maintenance of the tack in a desired location. Specifically, for example, where the tack is used in holding a first object such as a temporary covering to a second object such as cartilage, the tack's head and rod are buried in the cartilage, while the temporary covering is lodged between the transverse locking member and the cartilage. The back of the tack's conical head functions to hold the tack in the cartilage and prevents motion of the tack backwards out of the cartilage. The transverse locking member acts to hold the tack in the opposite direction and prevents the tack from moving forward through the temporary covering and into the cartilage. The covering is lodged in between the cartilage and the transverse locking member, such that the transverse locking member forms a seal between the cartilage and the covering. The offset transverse locking member is designed to pull the covering upward under it, thereby permitting the tacked covering to form a seal between the two objects which is much cleaner and closer to flush with the surface of the joined objects.

In some embodiments, the surgical fastener further comprises a ramp-like support that extends proximally and inwardly from the back side of the conical head to the elongate rod, thereby further supporting the conical head.

Insertion of the surgical fasteners is aided by the use of tack applicators. The tack applicators of the present invention preferably comprise an elongate handle, a loading tip, and a carrier assembly.

More particularly, the carrier assembly generally comprises body portion and a cannula extending from the front of the body portion. To aid in the handling of the small-sized tacks, the cannula of the carrier assembly is first used to grasp the rod portion of the tack. The cannula is provided with a slot on one side, from which the tail section, transverse locking member, and preferably the ramp-like support, all protrude. The conical head of the tack extends out and beyond the front of the cannula.

Preferably, the inner diameter of the cannula is sized to fit closely around the rod so as to engage the rod in a snug, frictional fit. In some embodiments, the tack further comprises at least one small bump on the outer surface of the cylindrical rod to aid in the frictional fit of the tack within the cannula. The outer diameter of the cannula is preferably sized to be less than or equal to the maximum diameter of the conical head of the tack, thereby minimizing the size of the insertion cut to the size of the conical head of the tack.

The loading tip of the tack applicator is designed to grasp onto the body portion of the carrier assembly from the proximal end, with the conical head of the tack extending out and beyond the distal or front end of the loading tip.

The elongate handle of the tack applicator may be straight or curved, in part to provide optimal access to various bodily cavities. In addition, to further aid in insertion of tacks into tight areas, the tack applicator preferably tapers from the back end of the elongate handle towards the loading tip.

The loading tip may further include a means for providing added visibility to a user during tack delivery. For example, such visibility means may include a window or a notch along the loading tip.

To aid a user's grip on the tack applicator handle, a portion of the handle may have a textured surface to prevent the applicator from slipping in one's hand.

Depending on the particular surgical procedure, the overall dimensions and shape of the tack applicator and carrier assembly may vary. For example, the tacks may be delivered either in an open procedure or arthroscopically, whereby arthroscopic procedures further involve the use of trocars, or other hollow delivery mechanisms, through which the various tools required during the repair may access the site. While the overall design of the tacks and the tack applicators is generally the same for both procedures, due to the nature of arthroscopic procedures, a narrower and longer applicator assembly is generally required for insertion through the hollow delivery mechanism.

In one embodiment, for arthroscopic tack delivery, the tapered handle of the tack applicator handle is longer and narrower than that for open procedures. In another embodiment, the carrier assembly for arthroscopic tack delivery is longer and narrower than the carrier assembly used in open surgery.

The carrier may further be made flexible along its length, for example, flexible plastic or kerfed material may be utilized to enable insertion of the tacks through a curved hollow delivery mechanism. The carrier preferably is further designed to help maintain proper orientation of the tack, so that, for example, the tack is not inadvertently inserted sideways or upside down. Thus, the carrier may have, for example, a rectangular or oval shaped cross section, or it may have a round or square cross section with a notch or raised area indicating the tack orientation.

To assist in holding and keeping track of numerous tack and carrier assemblies, a cassette may be provided which holds a plurality of carriers, each bearing a tack in position for use. The cassette generally comprises a number of parallel channels, each channel sized to fit and hold a carrier assembly. Preferably, the cassette is disposable.

The channels of the cassette are preferably divided into two columns, wherein one column holds new carrier assemblies with tacks loaded in the cannulas and the other column is for used carrier assembly disposal. Thus, after the tack is released from the cannula and into the body, the carrier assembly may be disposed of in the carrier assembly disposal column. This not only aids in sanitary disposal of used carriers, but also aids the surgeon in keeping track of th e number of tacks applied.

The channels of the cassette are preferably designed such that the tack's conical head is essentially at the front end of the channel with a space in front of the tack's head to protect the head, and a space located behind the back end of the carrier assembly. The channel is sized such that the tack applicator slides into the s pace behind the back end of the carrier assembly and in alignment with the carrier assembly, thereby ensuring proper loading of the carrier apparatus into the loading tip of the tack applicator. There may further be guides on the sides of each channel to further aid in proper insertion of the tack applicator.

The tack and tack applicator are generally used by the following procedure: a tack is first inserted into the cannula of the carrier apparatus, tail end first, until the tack is locked into place. The tail, ramp-like support and transverse locking member extend upwards out of the corresponding slot in the cannula. The sharp, conical head of the tack extends out and beyond the front of the carrier apparatus. The carrier assembly is then mounted into the loading tip of the tack applicator such that the back end of the carrier assembly is inserted first and the conical head of the tack extends out and beyond the entire tack applicator assembly. In the case where a cassette is used, the carrier assemblies with loaded tacks are preferably pre-mounted into one column of cassette channels. The tack applicator is simply pushed into a channel, with its loading tip first, until the loading tip engages and locks onto a carrier assembly. The tack applicator with the mounted carrier assembly is then withdrawn from the channel.

The tack is now ready for insertion into a desired site. The tack applicator is placed at the point of insertion with the sharp conical head of the tack leading the way. The tack applicator is pushed forward into the tissue as the sharp, conical head penetrates through the tissue. Once the tack has been pushed to the proper depth within the tissue, the tack applicator is gradually pulled out of the tissue. The tack's tail, transverse locking member, and back end of the conical head hold the tack securely in place within and in contact with the tissue, thereby disengaging the tack from the cannula of the carrier assembly, and preventing the tack from backing out of the tissue as the cannula is withdrawn from the tissue. Thus, the tack remains lodged within the tissue as the tack applicator is withdrawn.

Specifically, where the tack is used to repair cartilage and/or bone, the site is first prepared by methods known in the art. For example, all damaged or unhealthy cartilage is excised from the perimeter of the defect, the size of the defect is measured and a patch of natural or synthetic membrane, such as a periosteal patch, of appropriate size is placed over the defect. The tacks are then used to secure the patch over the defect by the tack insertion procedure outlined above. The use of small sized tacks is essential in such applications because the site being repaired is particularly thin and the cartilage at the site is often relatively soft. Further, attachment of the periosteal patch is made by inserting tacks about the outer perimeter of the patch close to the edges. Thus, the tack must not create too large of a hole which may pull and tear through the edge of the patch. The use of conventional tacks is not an option since such tacks will not fit within the site and since such tacks would potentially tear through the edges of the thin and delicate periosteum. Still further, previously known tacks are inappropriate for the periosteum and the like tissue because they are too rigid and resist bending, thereby causing additional stress and pain to the area.

More specifically, in the repair of damaged cartilage using Autologous Chondrocyte Implantation (ACI) treatment, see for example Brittberg et al, "Treatment of Deep Cartilage Defects in the Knee With Autologous Chondrocyte Transplantation", *New England Journal of Medicine*, 331:889–895 (Oct. 6, 1994) and Minas et al, "Chondrocyte Transplantation", *Operative Techniques in Orthopaedics*, Vol. 7, No. 4, pp. 323–333 (Oct. 1997), the fasteners, applicators and methods of the present invention are particularly suitable. The Autologous Chondrocyte Implantation (ACI) process has an advantage of restoring the articular surface of cartilage, for example in the knee, without compromising the integrity of healthy tissue or the subchondral bone. The Autologous Chondrocyte Implantation (ACI) process generally involves the following procedure: entering the knee to remove a biopsy of healthy cartilage tissue, which may then be cultured externally. The knee is again entered and the defect site is prepared by removing the damaged cartilage and measuring the lesion size. The cultured cartilage is then placed into the lesion and sealed off with a natural or synthetic membrane patch, such as a periosteum patch, using the tacks of the present invention. Within the lesion, the cells continue to multiply and integrate with surrounding cartilage. Over time, the cells continue to mature and fill in the lesion with healthy cartilage. In such a procedure, the features found in the present tacks are essential. Defects that qualify for Autologous Chondrocyte Implantation (ACI) treatment generally comprise a lesion surrounded by healthy cartilage, often called a focal chondral. Such defects involve relatively soft and thin cartilage. Further, the temporary patch utilized in such procedures is thin and delicate. Therefore, the use of small sized tacks is essential in such applications. Further, attachment of the temporary patch is made by inserting fasteners about the outer perimeter of the patch close to the edges of the patch. Thus, the tack must not create too large of a hole which may pull and tear through the edge of the patch. The presently available tacks are not suitable for such a delicate procedure due to their rigid, large structures. Such tacks are, rather, designed for adhering together two pieces of tough meniscal cartilage by inserting only a small number of large meniscal tacks through the central area of the meniscal cartilage. Typically the two pieces of meniscal cartilage being fixed together are similar in size, and, thus, the meniscal tacks must be large enough so that the tack extends through both pieces of the meniscus.

DETAILED DESCRIPTION OF THE INVENTION

Figure 1:
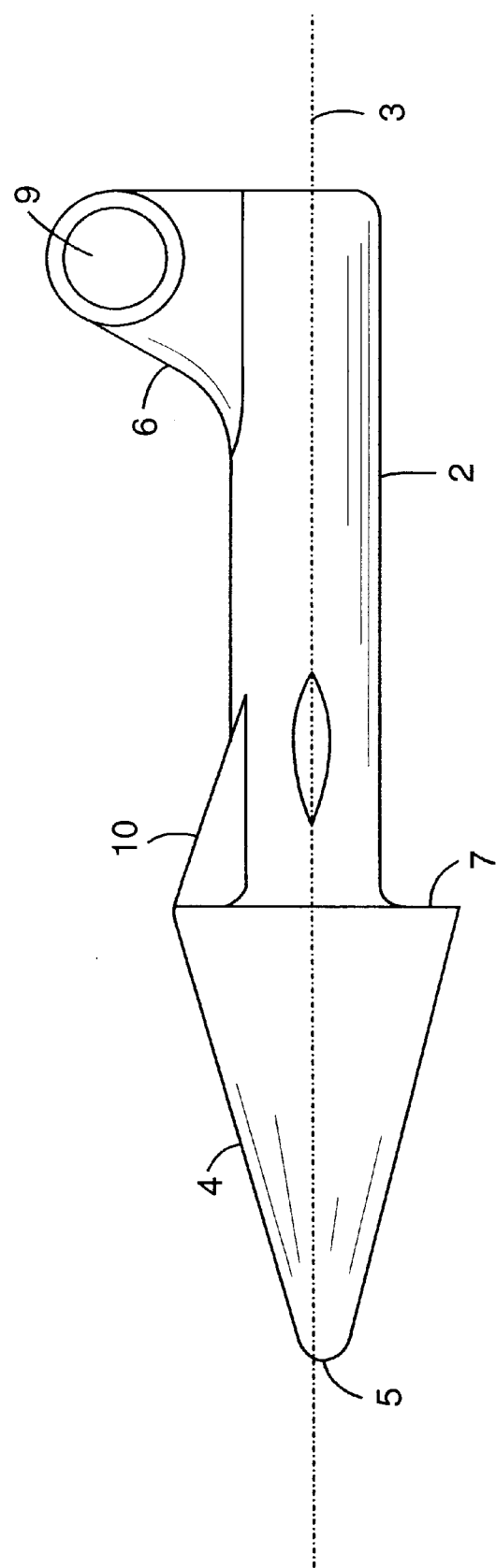
FIG. 1 shows a side view of a surgical tack in accordance with one embodiment of the present invention.
Figure 2:
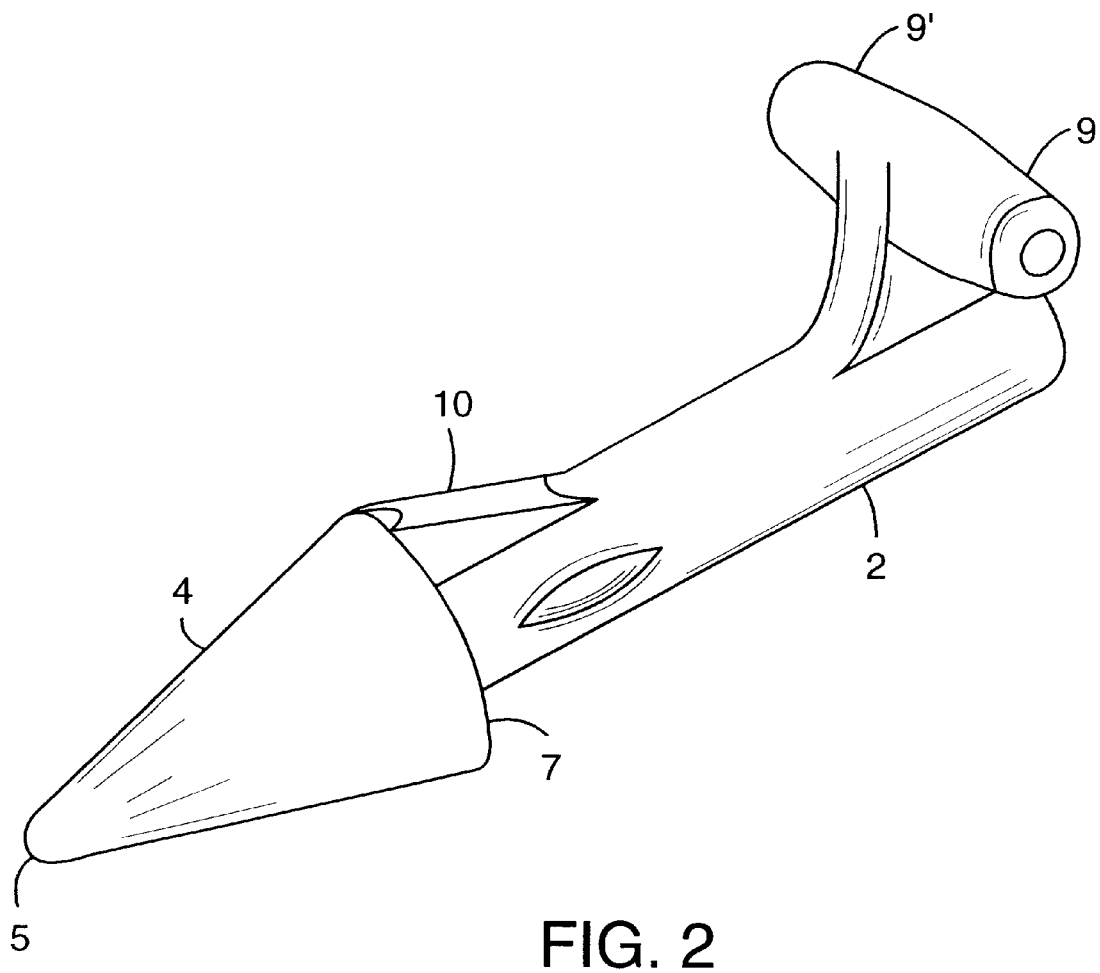
FIG. 2 shows a perspective view of the surgical tack shown in FIG. 1.
Figure 3:
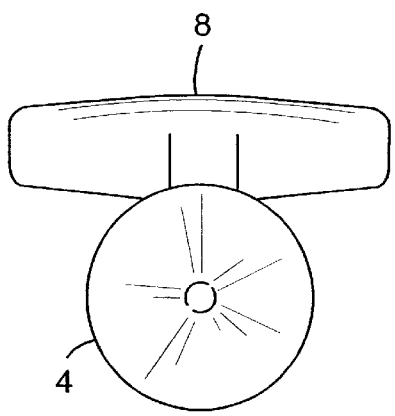
FIG. 3 shows a front view of the surgical tack of FIG. 1.
Figure 4:
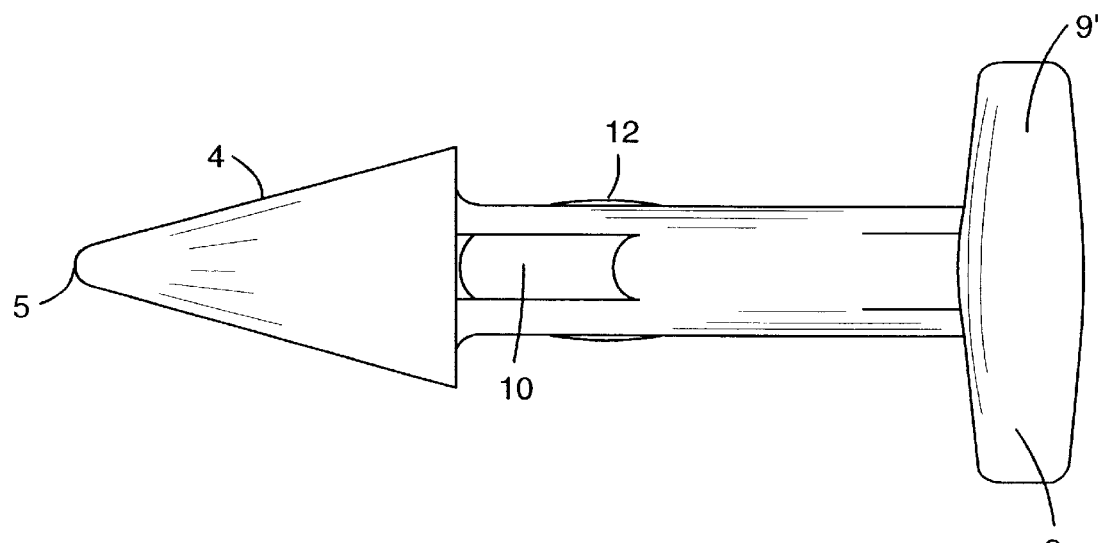
FIG. 4 shows a top view of the surgical tack of FIG. 1.

Referring now to the various figures of the drawing wherein like reference characters refer to like parts, there is shown in FIGS. 1–5 various views of a surgical tack 1 in accordance with the invention.

The tack 1 comprises a generally cylindrical rod 2, having at its distal end a sharp conical head 4 and at its proximal end a tail 6. The distal tip of the conical head is sharp, having the minum manufacturable radius of curvature, so that the cone can easily penetrate the tissue on which it is used. Preferably, the conical head 4 and the rod 2 share substantially the same longitudinal axis 3. The tail 6 preferably extends proximally and axially to the back end of the rod 6, and preferably extends from the rod to form a substantial angle with the longitudinal axis 3 of the rod 2.

Extending from the tail 6 is a transverse locking member 8. The transverse locking member 8 is offset from the longitudinal axis 3 of the rod 2 and head 4. Preferably, the transverse locking member 8 is formed by two generally symetrical protrusions 9 and 9' extending from opposite sides of the tail 6 in a direction transverse the longitudinal axis 3. The transverse locking member 8 is spaced from the surface of the rod 2.

Even more preferably, the protrusions 9, 9' are frustro-cylindrical in shape and rounded at their outermost extremities. Such a locking member 8, with protrusions 9, 9' extending transverse to the longitudinal axis of the rod 2 and head 4, is capable of effectively securing delicate and thin tissue, such as periosteal tissue, and prevents the tissue from slipping through the tack over the locking member 8. Further, the smooth surface of the frustro-cylindrical protrusions 9, 9' minimizes the potential for tearing in the tissue, a problem particularly encountered with thin tissue such as the periosteum. The protrusions may be of generally constant diameter or of varying diameter. For example, as shown in FIGS. 1–5, the protrusions 9, 9' may decrease in diameter from the tail 6 towards their outermost extremities.

Figure 5:
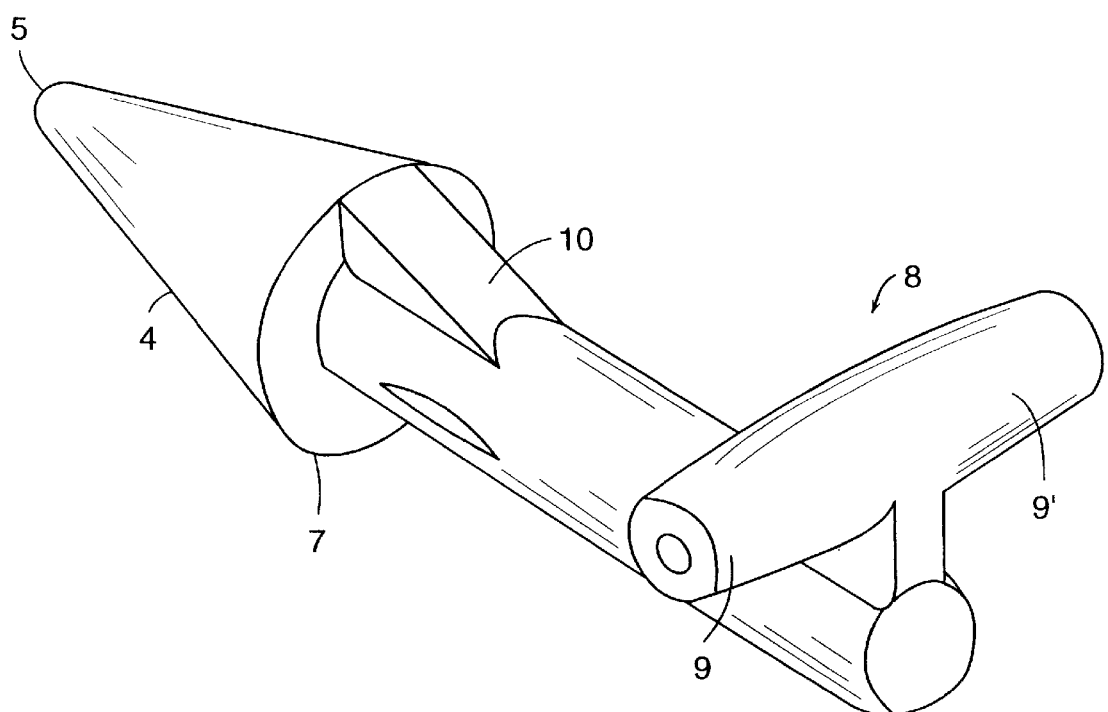
FIG. 5 shows a back perspective view of the surgical tack of FIG. 1.

The sharp conical head 4 has a front sharp end 5 and a back end 7 that is substantially flat and generally normal to the rod 2. The conical head 4 is sized such that the proximal end 7 thereof has a diameter greater than that of the rod 2, thereby extending beyond the rod 2 sufficiently to aid in holding the tack 1 in place within tissue and membrane upon delivery. The juncture between the proximal end 7 of the conical head and the rod 2 may be at a generally perpendicular sharp angle, or, as shown in FIGS. 1 and 5, the connection may form a smooth and slightly concave curve or fillet.

The tack preferably also includes a ramp-shaped support 10 that extends from the back end 7 of the conical head 4 and connects to the body 2, thereby providing further stability and support for the conical head 4. Most preferably, the ramp-shaped support 10 is a solid member that extends from the outermost diameter of the back end 7 of the conical head 4. As shown in FIG. 5, the ramp-shaped support 10 may have substantially angular edges or, alternatively, may have slightly rounded edges.

The tack 10 preferably has a maximum length of approximately 0.25 inch, more preferably a maximum length of about 0.2 inch, and even more preferably, a length in the range of about 0.12 to 0.16 inch. The rod preferably has a maximum diameter of approximately 0.03 inch, more preferably a maximum diameter of approximately 0.02 inch, and even more preferably in the range of about 0.015 to 0.017 inch. The maximum cone diameter is preferably about 0.05 inch, more preferably a maximum diameter of about 0.04 inch, and even more preferably in the range of about 0.029 to 0.033 inch. Preferably, the following combination of dimensions are used: rod length between about 0.12 to 0.13 inch, maximum rod diameter between about 0.015 to 0.017 inch, and maximum cone diameter between about 0.029 inch and 0.033 inch. Preferably, the maximum rod diameter is approximately ½ the maximum cone diameter. Thus, as the rod increases in size, the cone increases in size proportionally, and peferably, all other dimensions also increase proportionally. In an alternative preferred embodiment, the cone dimensions are enlarged by up to 50% while keeping all other dimensions of the tack constant.

The surgical tack 1 is preferably formed out of a bioabsorbable material. Bioabsorbable materials are known in the art and include materials such as polyglycolic acid, polylactic acid, polydioxanone, polycaprolactone, trimethyl carbonate and copolymers thereof. Because a tack applicator is used to hold the rod of the tack rigid during insertion, less rigid, more rapidly degrading bioabsorbable polymers may be used. Thus, a more comfortable and flexible tack, which does not resist bending, and which is absorbed more quickly by the body, may be fabricated.

FIGS. 6–7, 10–13 and 22–25, depict various views of tack applicators 20 in accordance with the invention. The use of tack applicators 20 aids in holding the small sized tacks and aids in proper alignment and placement of the small sized tacks.

Figure 6:
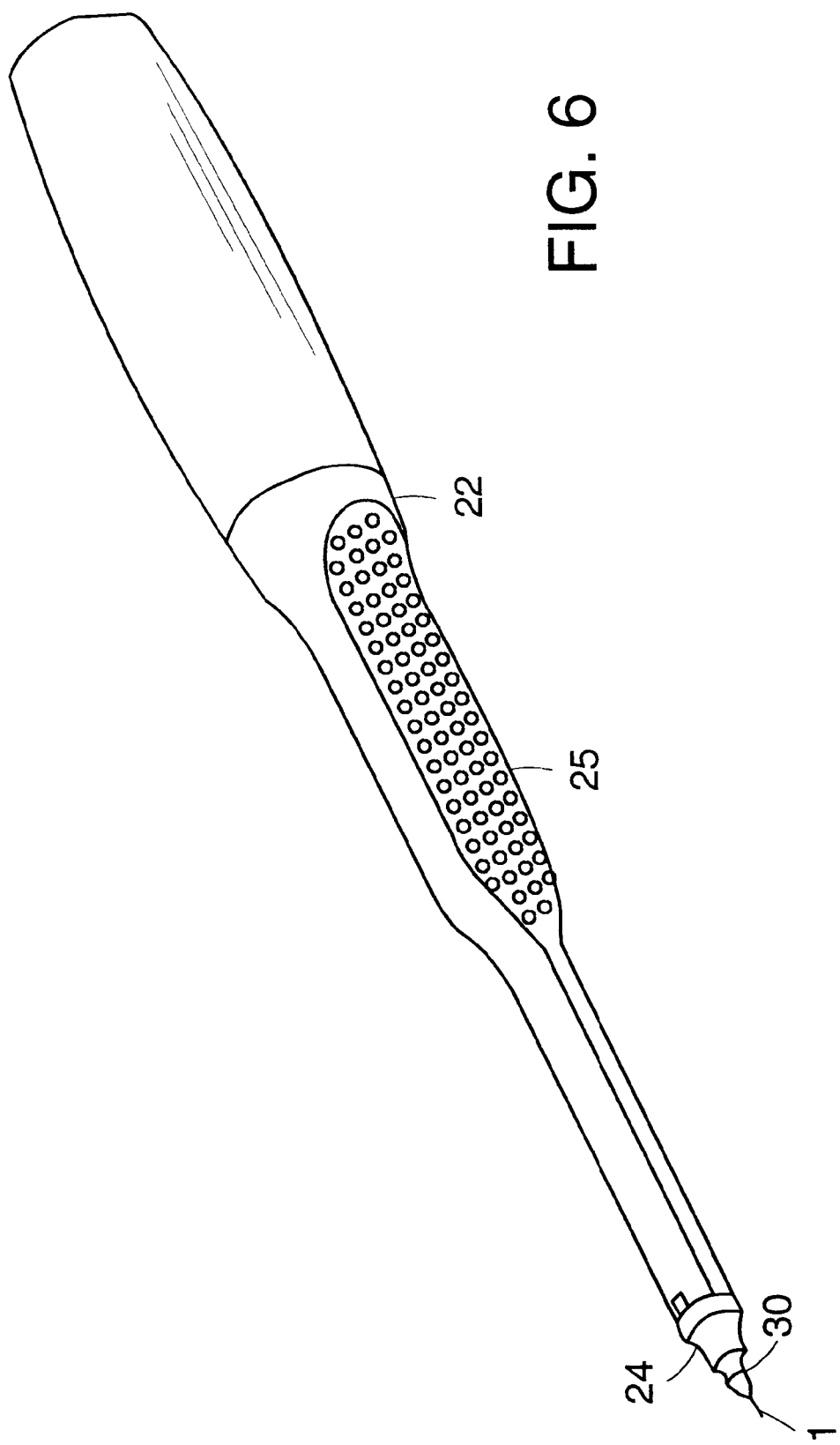
FIG. 6 shows one embodiment of a tack applicator in accordance with the present invention.
Figure 7:
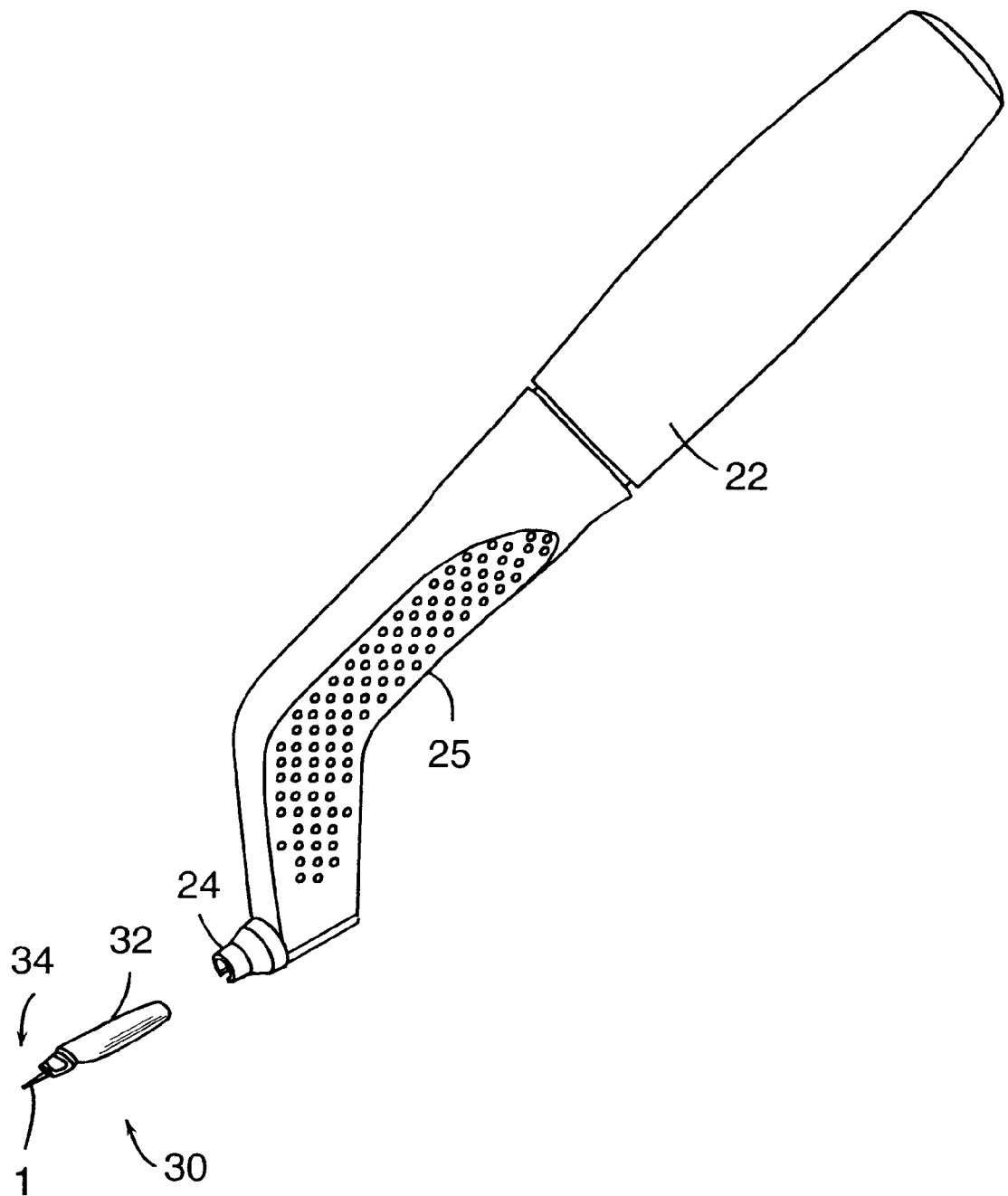
FIG. 7 shows a second embodiment of a tack applicator in accordance with the present invention.
Figure 10:
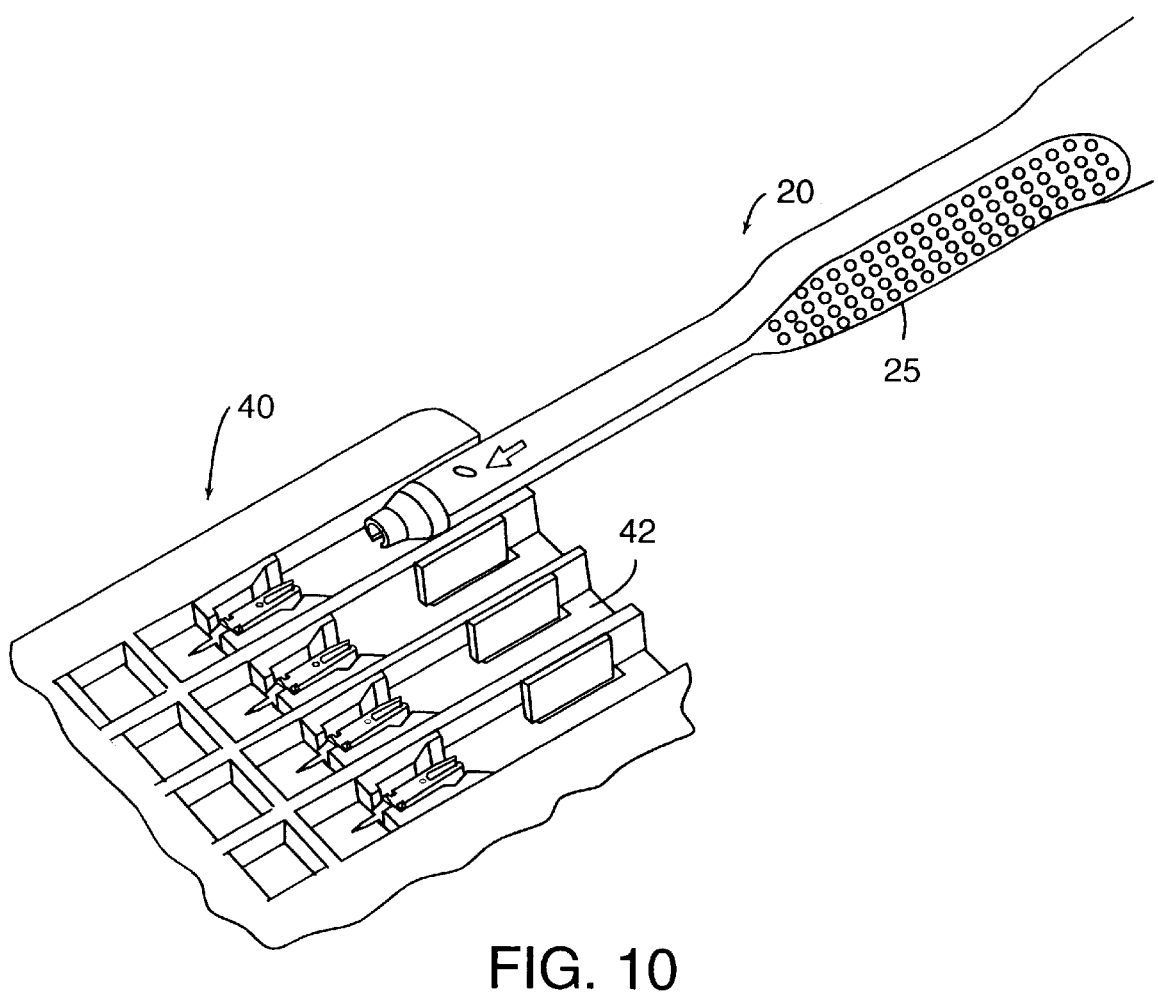
FIG. 10 shows the tack applicator being inserted into the cassette for carrier assembly loading.
Figure 11:
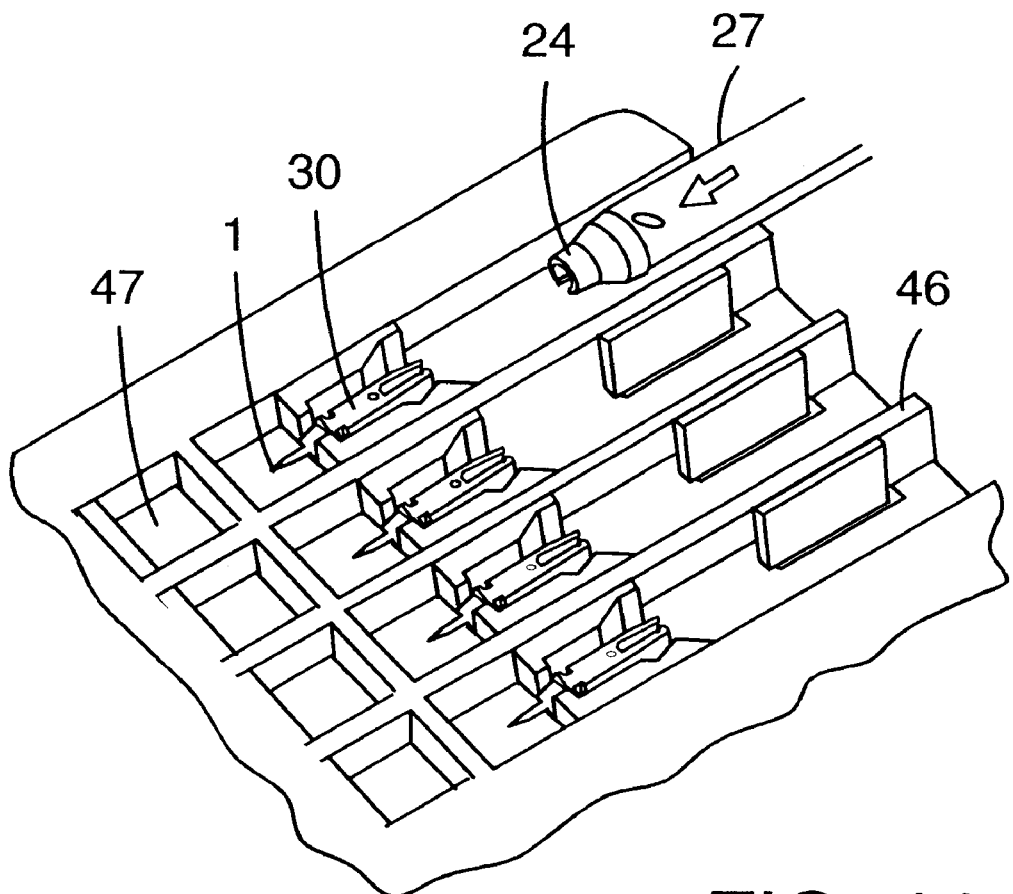
FIG. 11 shows an enlarged view of FIG. 10.
Figure 12:
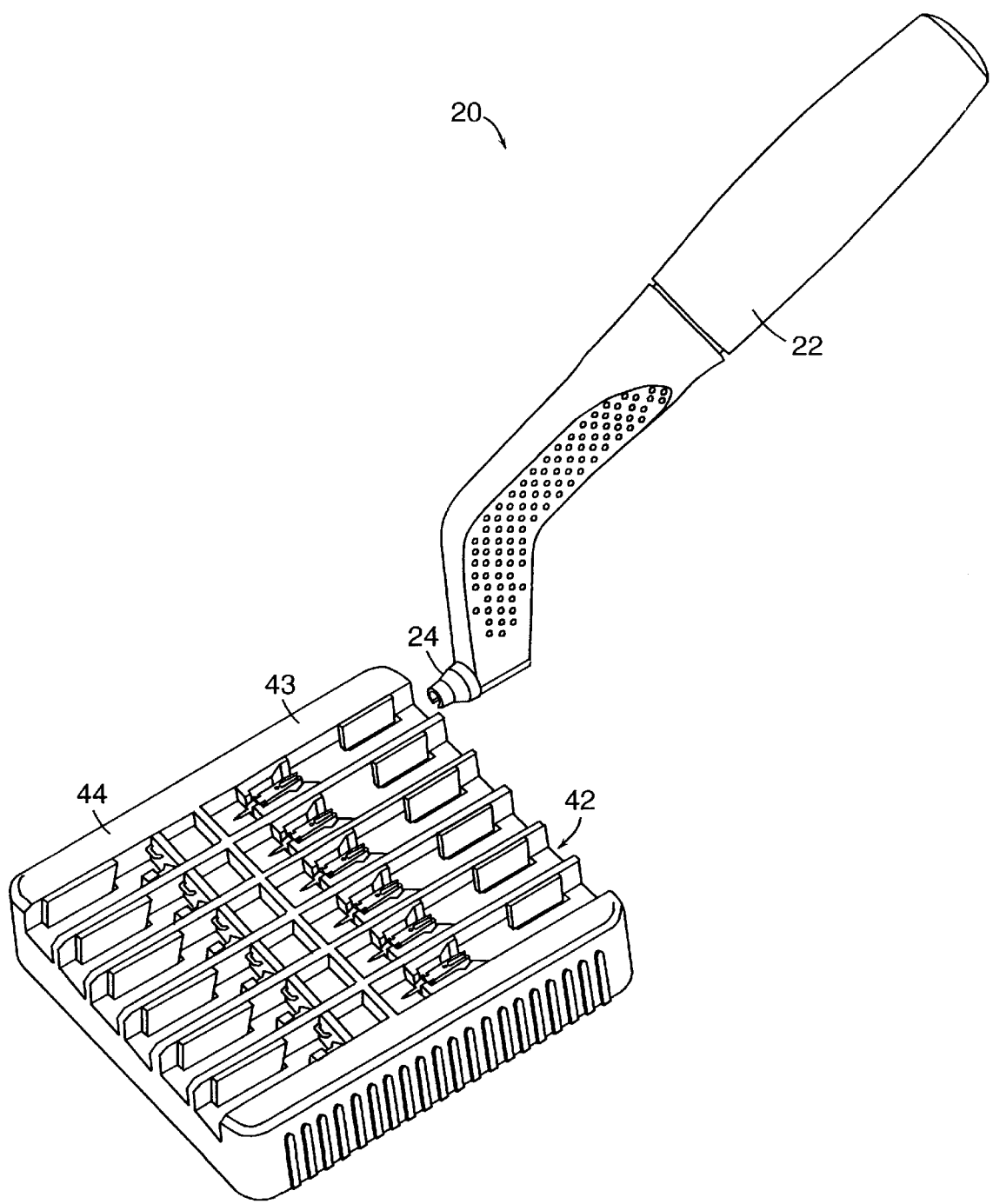
FIG. 12 shows a curved handled tack applicator and the cassette for carrier assembly loading.
Figure 13:
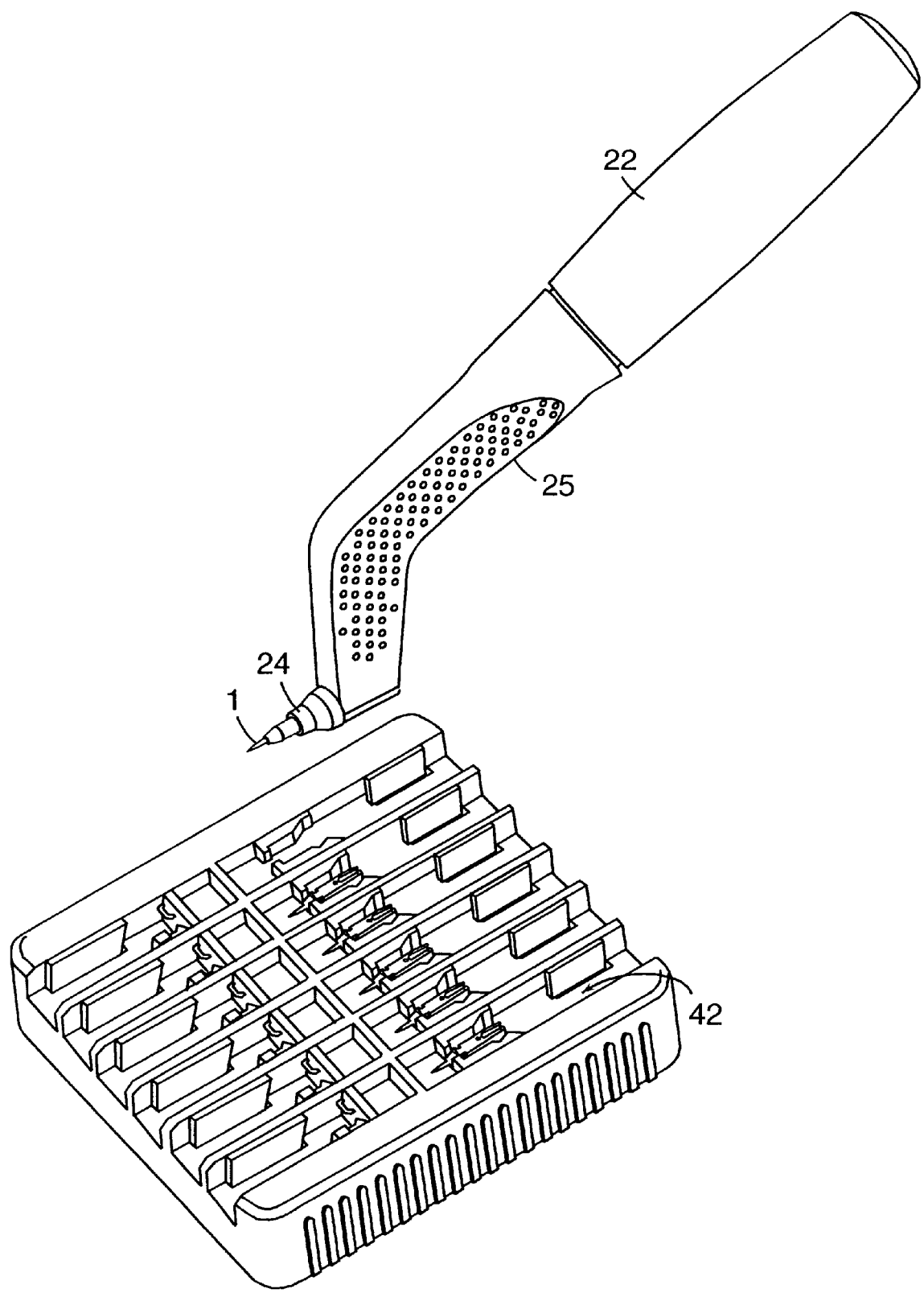
FIG. 13 shows a cassette and a curved handled tack applicator with a loaded carrier assembly.

The tack applicators 20 comprise in general an elongate handle portion 22 and a loading tip 24. The handle portion 22 is designed to provide and individual with a comfortable and steady grip, and is preferebly an elongate member. The handle may be substantially straight as shown in FIG. 6, 10 and 11 or it may be curved in part as shown in FIGS. 7, 12 and 13, to provide enhanced accessibility into certain areas of the body. As seen in the figures, the handle 22 preferably tapers towards the loading tip 24 to provide better access into tight areas.

There may further be included, along the handle 22 towards the loading tip 24, a textured surface 25 that one may use to enhance one's grip on the tack applicator 20. Generally, the upper portion of the handle 22 would be enclosed in one's palm, while one's fingers, particularly the thumb and pointer finger, may rest on the textured surface 25.

As shown in FIGS. 6 and 7, a carrier assembly 30 is removably mounted in the loading tip 24. The carrier assembly 30 assists in the handling and proper alignment of the small sized tacks 1 within the tack applicator 20, and comprise generally a body portion 32 and a cannula 34.

Figure 9:
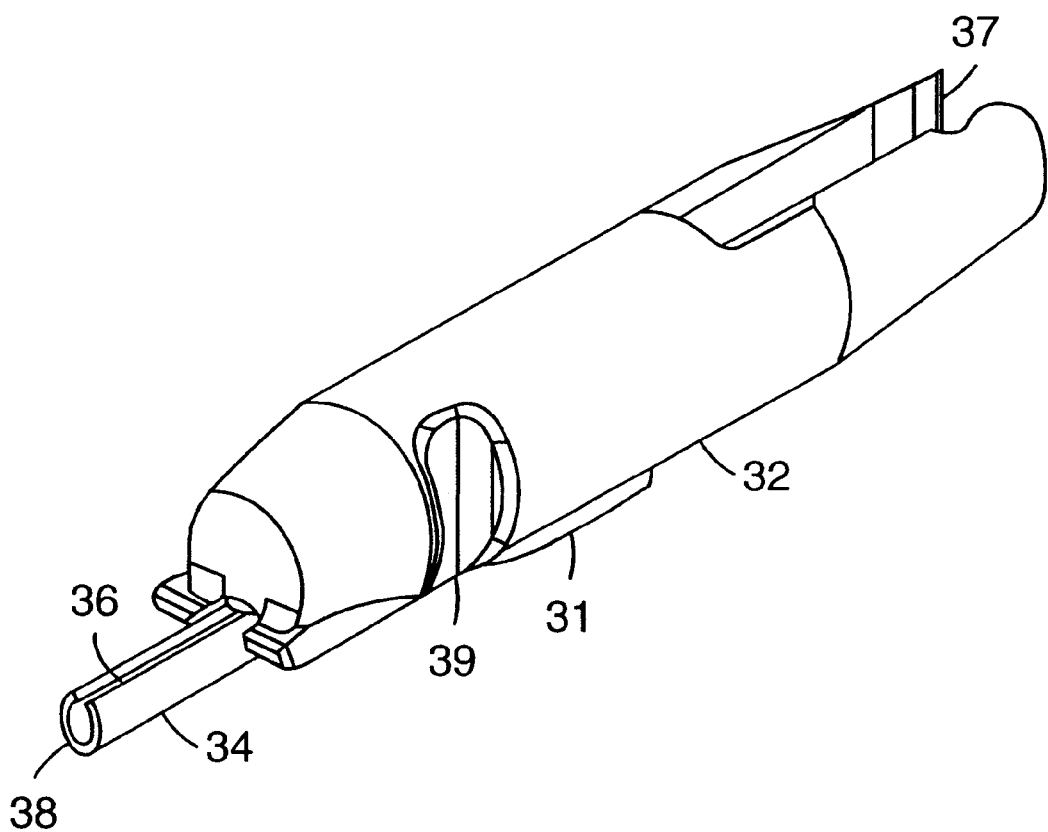
FIG. 9 shows an enlarged view of one embodiment of a carrier assembly in accordance with one embodiment of the present invention.
Figure 9B:
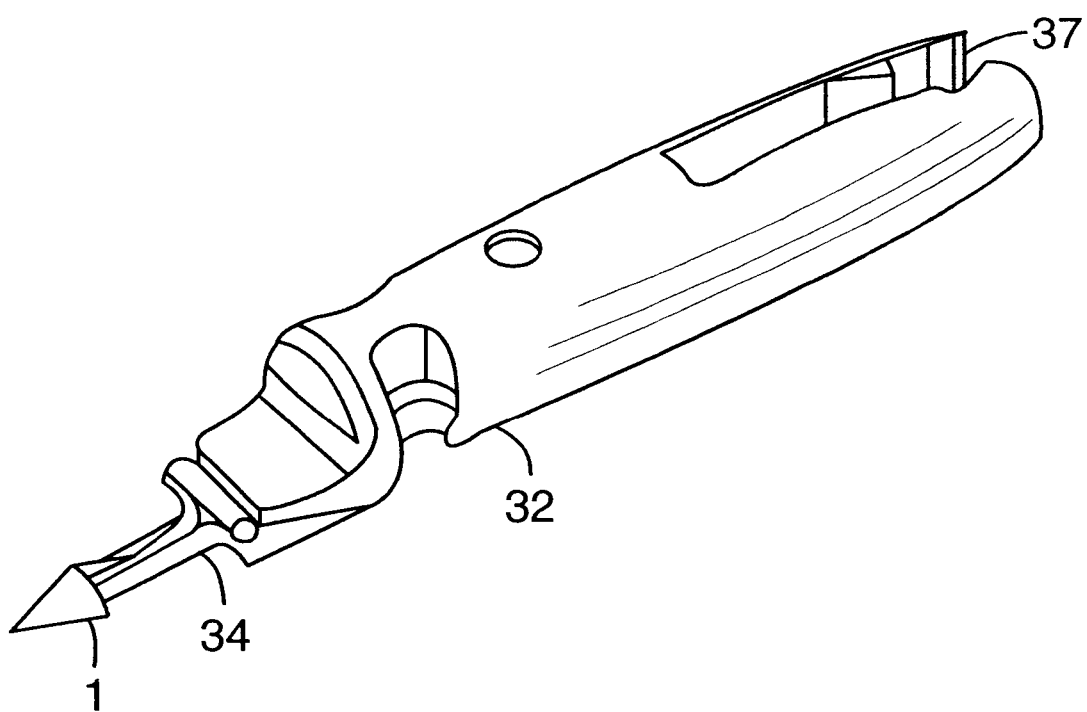
FIG. 9b shows an enlarged view of one embodiment of a carrier assembly holding a tack in accordance with the present invention.

The cannula 34 extends from the front of the body portion 32, and is the portion of the carrier assembly 30 that holds the tack 1. As shown in FIG. 9b, the cannula 34 of the carrier assembly 30 grasps the rod 2 of the tack 1. The cannula 34 is provided with at least one slot 36 corresponding to the tack's ramp-like support 10, tail 6, and transverse locking member 8. The tack 1 fits within the cannula 34 and is held by a frictional fit. The tack 1 may further contain at least one small bump 12 on the rod 2 to further aid in the gripping of the tack 1 by the cannula 34. The bump 12 preferably designed with a maximum height away from the rod surface of approximately 0.004 inch, more preferably a maximum height of approximately 0.003 inch, and even more preferably in the range of about 0.0015 to 0.0025 inch. Preferably, the maximum height of the bump 12 is approximately ⅒ to ¹⁄₁₄ of the maximum rod diameter.

Figure 21:
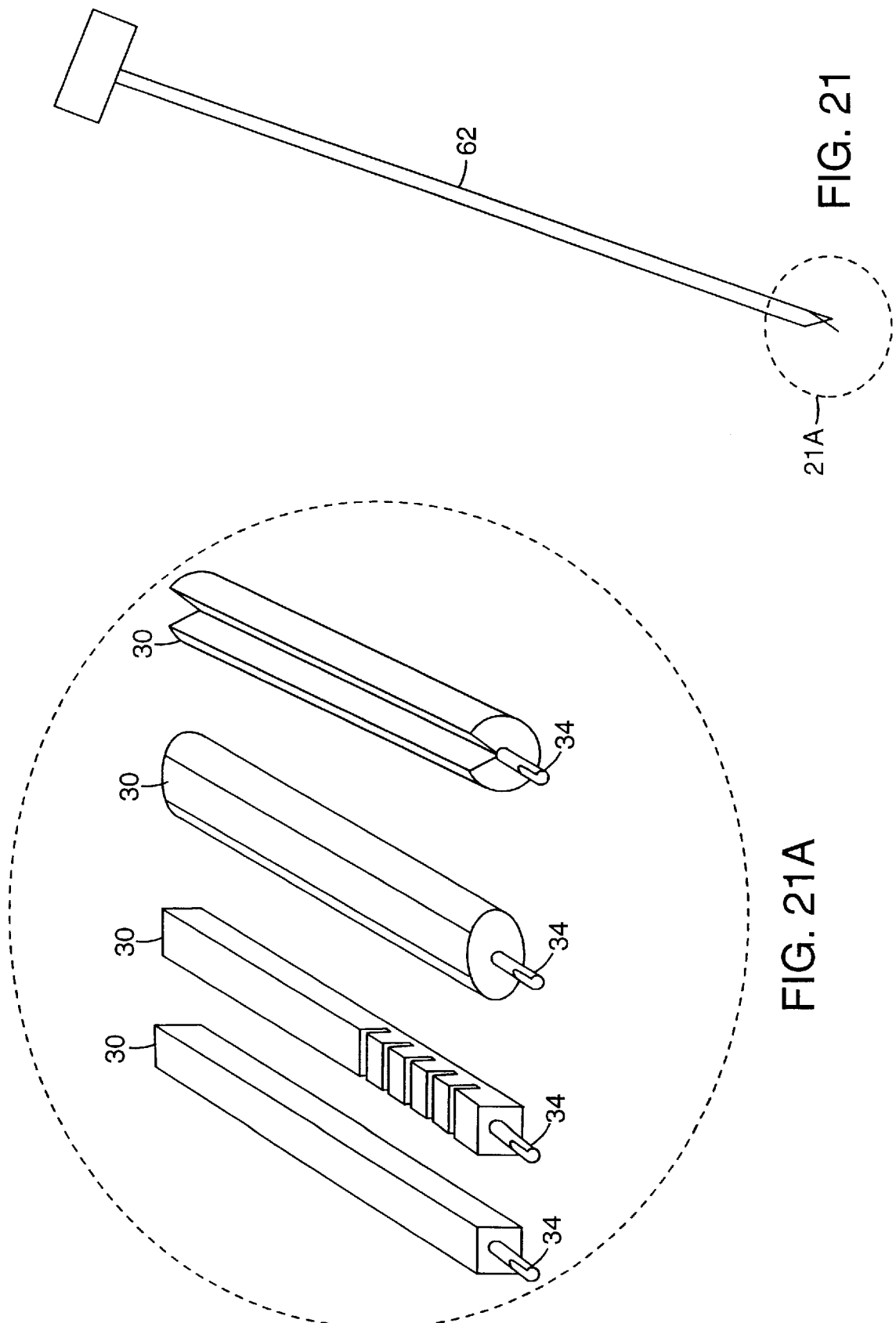
FIG. 21 shows various carrier assembly embodiments in accordance with the present invention as used in arthroscopic procedures.

The cannula 34 further contains an opening 38 at its front end through which the sharp conical head 4 extends out and beyond the front of the cannula 34, as shown in FIG. 9b. In some embodiments, the cannula 34 has an overall cylindrical shape with a circular cross section, as shown in FIGS. 9 and 11. However, the cannula 34 may alternatively have a square, rectangular or oval cross section as shown in FIG. 21. Preferably, the inside of the cannula is cylindrical to correspond to the tack's cylindrical rod 3. In its preferred form, the cannula 34 is sized such that it has an inner diameter sized to engage the tack in a frictional fit with the cannula 34, and an outer diameter or width that is sized no greater than the maximum diameter of the conical head 4. This provides the additional advantage of minimizing trauma to the area of insertion by limiting the size of the cut through the tissue to the conical head 4 of the tack 1. Thus, while the tack applicator 20 provides the advantage of aiding in the insertion of the tack by pushing the tack 1 through the tissue by the front end of the cannula 34 pushing on the back end 7 of the conical head 4, at the same time, the cannula 34 does not add any thickness to the cut made during insertion. Thus, during application, the walls of the cannula provide the rigidity along the tack's length, and rod 2 can be a flexible connector between the head 4 and the transverse locking member 8. Prior attachment devices required a rigid shaft between a penetrating end and a base portion so that the device could be inserted into the tissue.

The loading tip 24 grasps and locks onto the back of the body portion 32 of the carrier assembly 30. The body portion 32 may fit within the loading tip 24 by any means. For example, as shown in FIG. 9, a frictional fit may be aided by at least one groove 37 in the back of the carrier assembly body portion 32 that corresponds to a protrusion within the loading tip 24 that fits and locks within the groove 37. As shown in FIG. 9, there may further be a protrusion 31 along the body 32 of the carrier assembly 30, which may fit within a corresponding slot in the loading tip to aid in proper alignment of the carrier within the loading tip 24. Such an arrangement also helps to keep the carrier assembly 30 from rotating within the loading tip 24.

As shown in FIGS. 7 and 13, the carrier assembly 32 is preferably inserted within the loading tip 24 such that a substantial part of the carrier body portion 32 is within the loading tip 24 for increased hold and stability. The cannula 34 and the tack 1 extend out the front of the loading tip 24 and beyond the front of the tack applicator 20.

Figure 22:
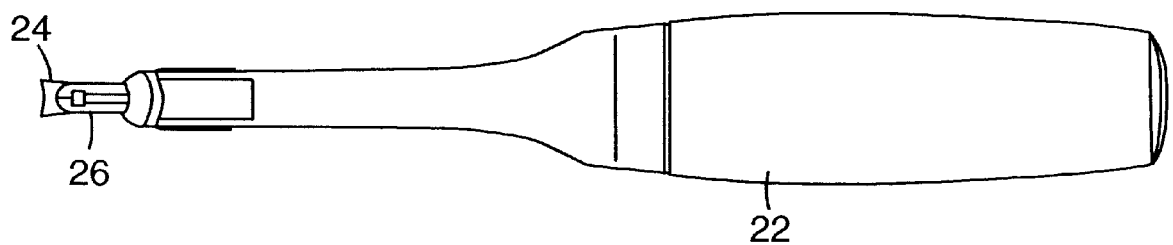
FIG. 22 shows a top view of one embodiment of a spring loaded tack applicator of the present invention.
Figure 23:
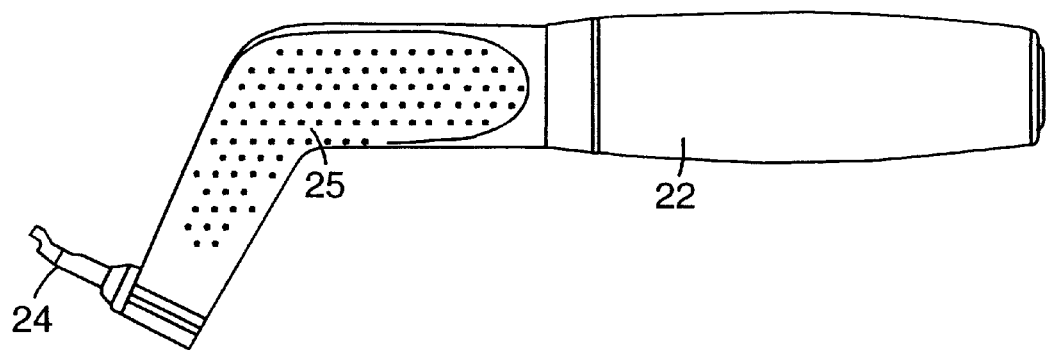
FIG. 23 shows a side view of the tack applicator of FIG. 22.
Figure 24:
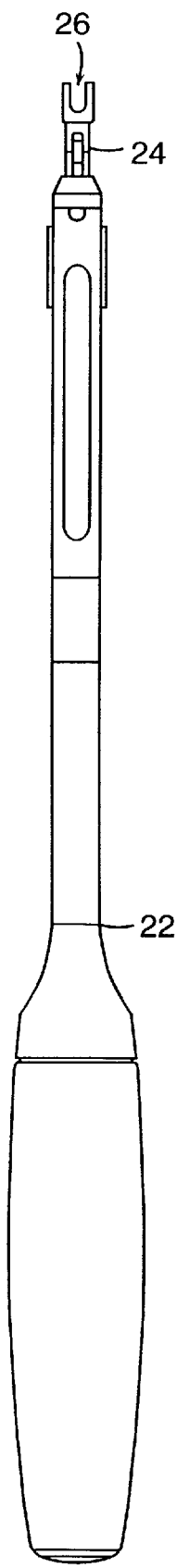
FIG. 24 shows a top view of a second embodiment of a spring loaded tack applicator of the present invention.
Figure 25:
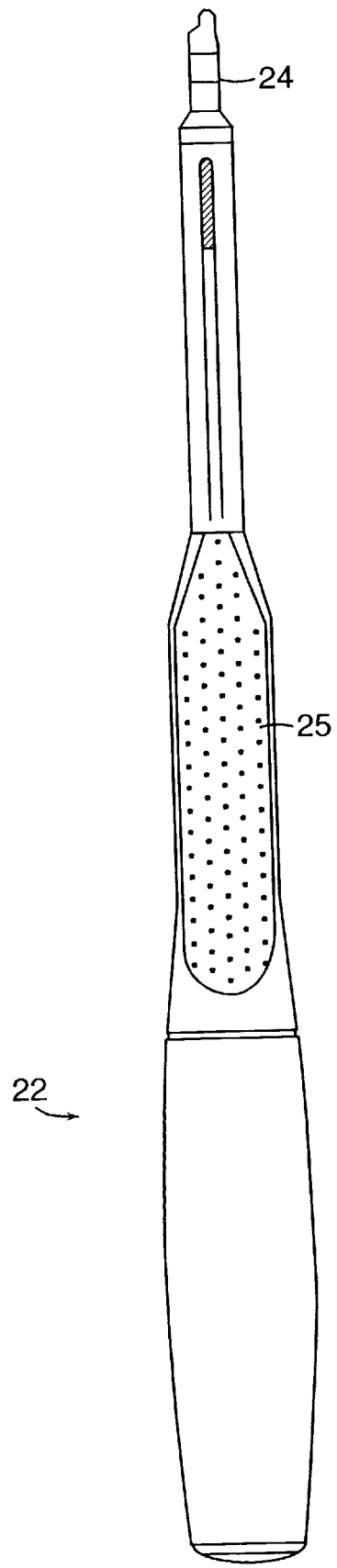
FIG. 25 shows a side view of the tack applicator of FIG. 24.
Figure 29:
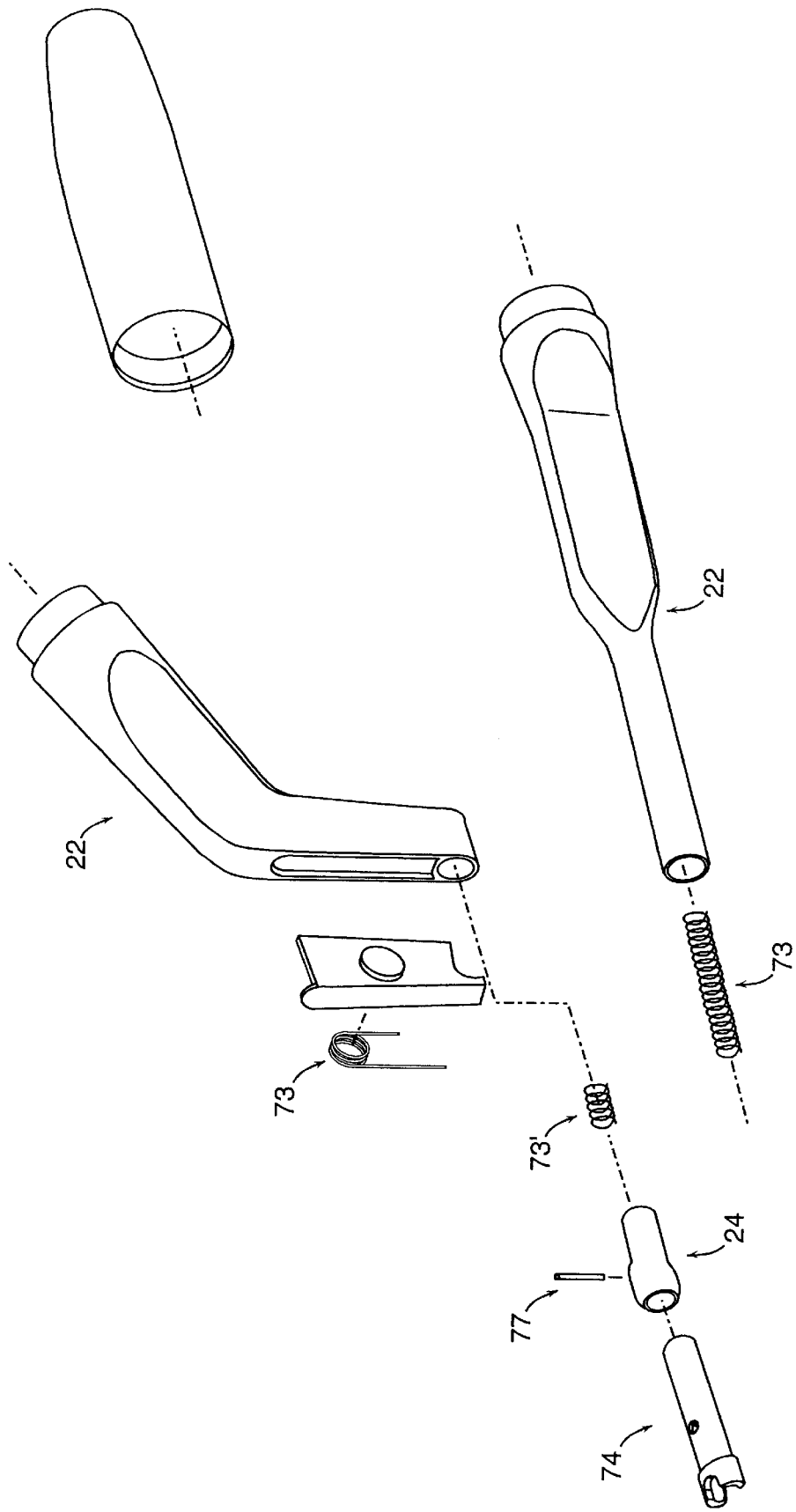
FIG. 29 shows one embodiment of the spring assembly as mounted within a straight handled tack applicator and one embodiment of the spring assembly as mounted within a curved handled tack applicator in accordance with the present invention.

In some applications, a tack viewing means 26 and spring loading mechanism may be located in the tack applicator 20 to provide a user with a view of the tack being inserted and to aid in tack insertion to a proper depth. The viewing means 26 may be, for example, a window or notch as shown in FIGS. 22 and 24. The viewing means 26 is preferably located within a guide mechanism 74 that is preferably included in the spring loaded tack applicators, as shown in FIG. 29.

Figure 26:
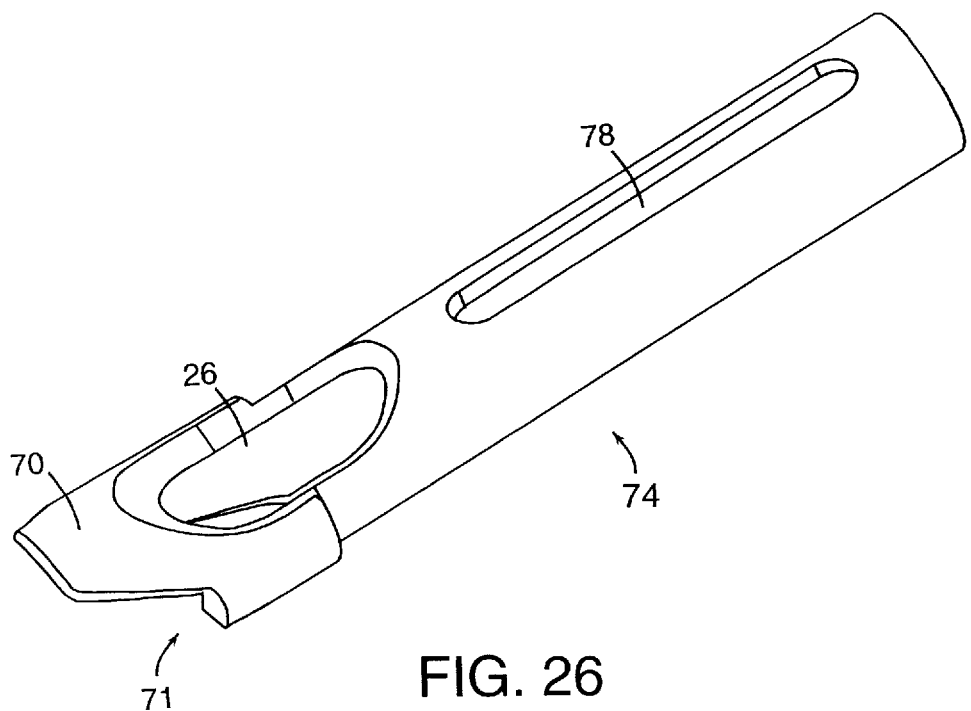
FIG. 26 shows an isometric view of one embodiment of the tack applicator tip having a window in accordance with the present invention.
Figure 27:
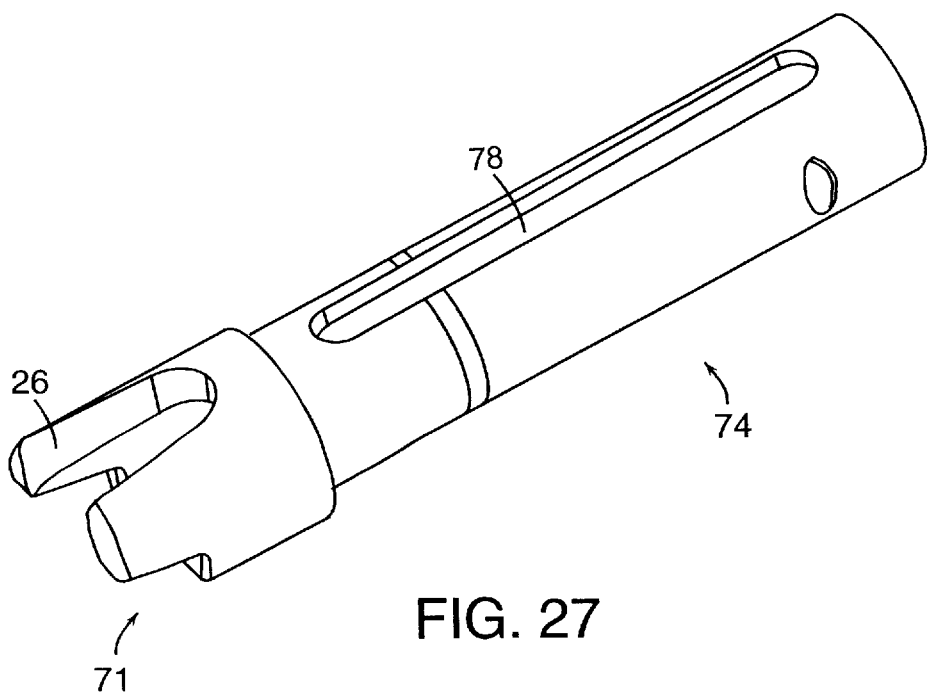
FIG. 27 shows an isometric view of one embodiment of the tack applicator tip having a notch in accordance with the present invention
Figure 28:
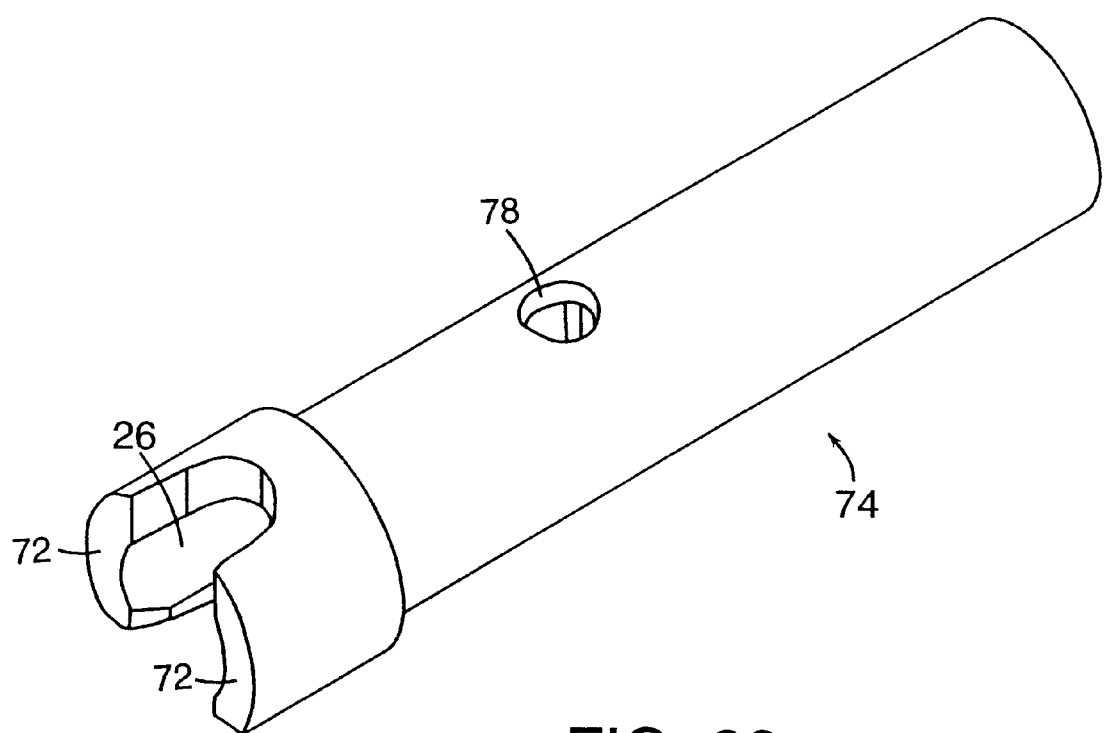
FIG. 28 shows an isometric view of a second embodiment of the tack applicator tip having a notch in accordance with the present invention

Enlarged views of the viewing means 26 in the guide mechanism 74 are shown in FIGS. 26–28.

In one embodiment, as shown in FIG. 26, window 26 is located within the guide mechanism 74 as shown. The guide mechanism 74 is preferably designed with a top extension 70 and a bottom bumper portion 71 for seating against the exterior surface as the tack 1 is inserted. Preferably, the bumper portion 71 holds the periosteal patch against the cartilage securely as the tack 1 is inserted. The tack 1, when loaded, would be located below the window 26. As the tack is inserted, the tack 1 passes across under the window.

In a second embodiment, as shown in FIG. 27, notch 26 may be located within the guide mechanism 74 as shown. The notch is particularly useful in that a holding tool, such as forceps, may be inserted through the notch to hold the periosteal patch steady as the tack 1 is being inserted. A bottom bumper portion 71 like that described in FIG. 26 may also be included in this embodiment.

In a third embodiment, as shown in FIG. 28, a notch is located in the guide mechanism 74 as shown. Again, a holding tool, such as forceps, may be inserted through the notch to hold the periosteal patch steady as the tack 1 is being inserted. In this embodiment, there may further be side bumper portions 72 for seating against the exterior surface, as the tack 1 is inserted, to prevent the applicator 20 from entering the tissue.

To ensure proper depth of insertion and to aid in gradual withdrawal of the tack 1 from the cannula 34 as the tack applicator 20 is withdrawn from the site, a spring mechanism may further be located within the tack applicator 20. The spring mechanism is preferably designed such that the spring 73 is fully extended when the tack 1 is loaded the loading tip 24. Upon pushing the tack 1 into the tissue, the spring 73 compresses until it is fully compressed, while détente spring 73' prevents further movement of the guide mechanism 74. Once the spring 73 is fully compressed, the bottom bumper portion 71 of the guide mechanism 74 maintains the applicator 20 external to the tissue and prevents further pushing of the tack 1 into the tissue. The spring 73 further aids in a more gradual withdrawal of the cannula 34 from the site without withdrawal of the tack 1.

Two embodiments of a spring mechanism are shown in FIG. 29 by cut-away views of the interior portions of the tack applicator 20. As shown, the spring 73, 73' is located within the tapered portion of the tack applicator handle 22. The spring 73 is located behind the loading tip 24, which holds the guide mechanism 74. Thus, as the tack 1 is inserted into the tissue, pressure is applied to the tack, which in turn applies pressure to the carrier assembly 30. The carrier assembly 30 holding the tack 1 is pushed backwards as the spring 73 compresses. Once the spring 73 is fully compressed, the tack 1 has reached its maximum depth and the tack applicator 20 cannot push the tack 1 in any deeper. Also, once detente spring 73' is fully compressed, the guide mechanism 74 cannot be pushed back into the tack applicator 20 any further. At this point, the tack applicator 20 is pulled backwards. As this occurs, the pressure of the tack 1 against the carrier assembly 30 is reduced, which in turn allows the spring to expand back to its fully extended position. Thus, as the tack applicator 20 holding the carrier assembly 30 is pulled backwards away from the tack 1, the spring and the attached carrier assembly 30 with the cannula 34 is allowed to extend towards the tack 1 a bit, thereby making the removal of the tack 1 from the cannula 34 less abrupt.

As shown in FIG. 29, in addition to spring 73, there may further be included a détente spring 73'. The combination of the two springs act together to compress within the tack applier 20 and ensure proper insertion depth of the tack 1. Alternatively, a single free-floating spring 73 may be used. Preferably, these springs 73, 73' are located behind a guide 74 and loading tip 24 assembly which holds the carrier assembly 30. Thus, as pressure is applied the the carrier assembly 30, the guide 74 and loading tip 24 assembly pushes on the spring 73, 73' to compress it.

For example, as shown in FIG. 29, the loading tip 24 may seat against the spring 73. The guide mechanism 74 may then be attached to the loading tip 24, for example, by sliding through a hole in the loading tip 24. Further, a pin 77 may be inserted through the loading tip 24 and guide mechanism 74 to hold the pieces together. The pin 77 may further hold the carrier assembly 30 within the loading tip 24 by fitting within the notch 37 in the back of the carrier assembly 30. The pin may fit through either a slot 78 in the guide mechanism 74, shown in FIGS. 26 and 27 or a hole 78 in the guide mechanism 74, shown in FIG. 28, to hold the pieces 74 and 24 together. The hole 78 in FIG. 28 holds the guide mechanism 74 stationary within the loading tip 24. The slot 78 in FIGS. 26 and 27 allows the guide mechanism 74 further range of motion within the loading tip 24, thereby providing additional compression of the carrier assembly 30 after the spring has been completely compressed.

For convenience, a number of carrier assemblies 30 and tacks 1 may be mounted in a cassette 40 for easy loading and disposal of the new and used carrier assemblies 30. Various views of the cassette 40 are shown in FIGS. 8, 8b and 10–13. The cassette 40 is preferably disposable and contains a number of parallel channels 42.

These channels 42 may be divided into two columns, wherein one column 43 is for new carrier assembly pickup and the other column 44 is for used carrier assembly disposal. Thus, after the tack 1 is released from the cannula 34 and into the tissue, the carrier assembly 30 may be disposed of by loading it into the disposal column 44.

The channels 42 of the cassette 40 are preferably designed such that the tack's conical head 4 is essentially at the front end of the channel 42, and a space is located behind the back end 37 of the carrier assembly's body portion 32. Further, as shown, the tack's head 4 is protected by leaving a sufficient opening 47 in front of the carrier assembly. Still further, as shown in FIG. 8b, a flap 48 may be included, which extends completely or partially over the opening 47 in the pickup channel 43, thereby covering the tack and providing an added safety feature. As a user pushes the tack applicator 20 into the pickup channel 43, the flap 48 prevents the user from pushing straight through the channel and puncturing himself or another with the tack. 1.

The carrier assemblies 30 may be held securely within the channels 42 by the groove 37 in the carrier assembly body portion 32, as shown in FIGS. 10–13. As shown in FIG. 9, there may also be at least one indentation 39 in the sides of the carrier assembly's body portion 32 to further lock the carrier assembly 30 within the channels 42 as shown in FIGS. 10–13. This is accomplished by providing a number of protrusions in the channels 42 which fit and lock into the groove 37 and the indentations 38.

The channels 42 are preferably designed such that the tack applicator 20 slides into the space behind the carrier assembly 30 and in alignment with the carrier assembly 30, thereby ensuring proper loading of the carrier assembly 30 into the loading tip 24 of the tack applicator 20. Thus, one may simply push the tack applicator 20 into a channel 42 until the loading tip 24 engages and locks onto a carrier assembly 30. To further aid in proper insertion of the applicator 20 and proper pick-up of the carrier assembly 30, guides 46 may be located along the channel edges such that the tack applicator 20 slides underneath the guides 46 in alignment with the carrier assembly 30. Still further, corresponding notches 27 may be located on the edges of the tack applicator 20 to further aid in proper alignment of the tack applicator 20 in the channel 42. Once the carrier assembly 30 is loaded into the loading tip 24, the tack applicator 20 is then withdrawn by lifting it from the channel 42 with the carrier assembly 30 correctly locked into the loading tip 24.

The surgical tack 1 and tack applicator 20 may be used to approximate and fix tissue and membranes quickly and accurately during surgical procedures. The following procedure is generally used:

The surgical tack 1 is loaded into the cannula 34 of the carrier assembly 30 by sliding the tack into the cannula 34, back end first, such that the tail 6, transverse locking member 8, and ramp-like support 10 extend from the corresponding slot 36 and the tack 1 is preferably frictionally held in place within the cannula 34, with the leading edge of the cannula adjacent the proximal end 7 of the conical head 4, as best seen in FIG. 13. Next, the carrier assembly 30 is mounted into the loading tip 24 of the tack applicator 20 with the back end 37 of the body portion 32 first, such that a substantial portion of the carrier assembly 30 body portion 32 is held and locked within the loading tip 24, with the cannula 34 and tack 1 extending out of and in front of the loading tip 24, as best seen in FIGS. 7 and 13.

Figure 8:
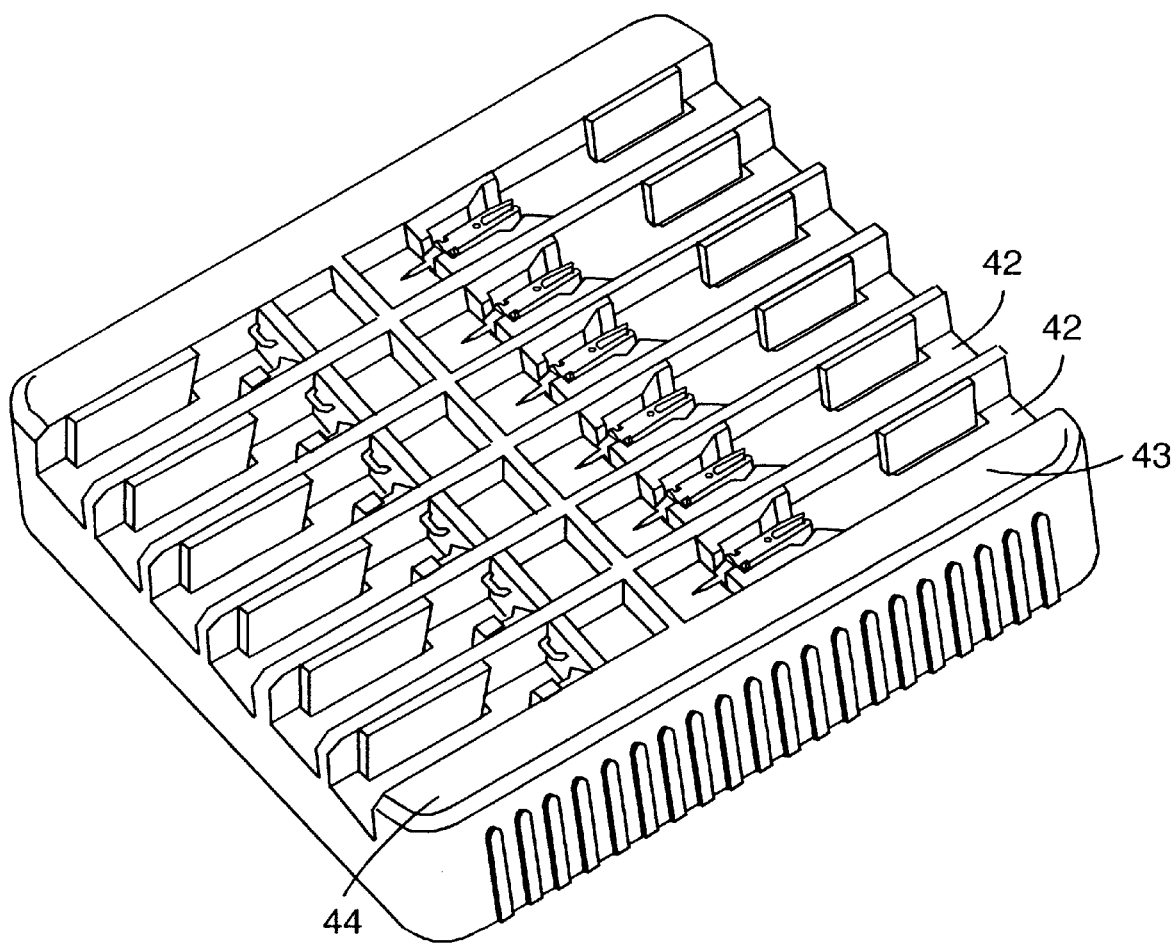
FIG. 8 shows a perspective view of a carrier cassette assembly holding a number of carriers provided with surgical tacks ready to be picked up by a tack applicator and used in accordance with the present invention.
Figure 8B:
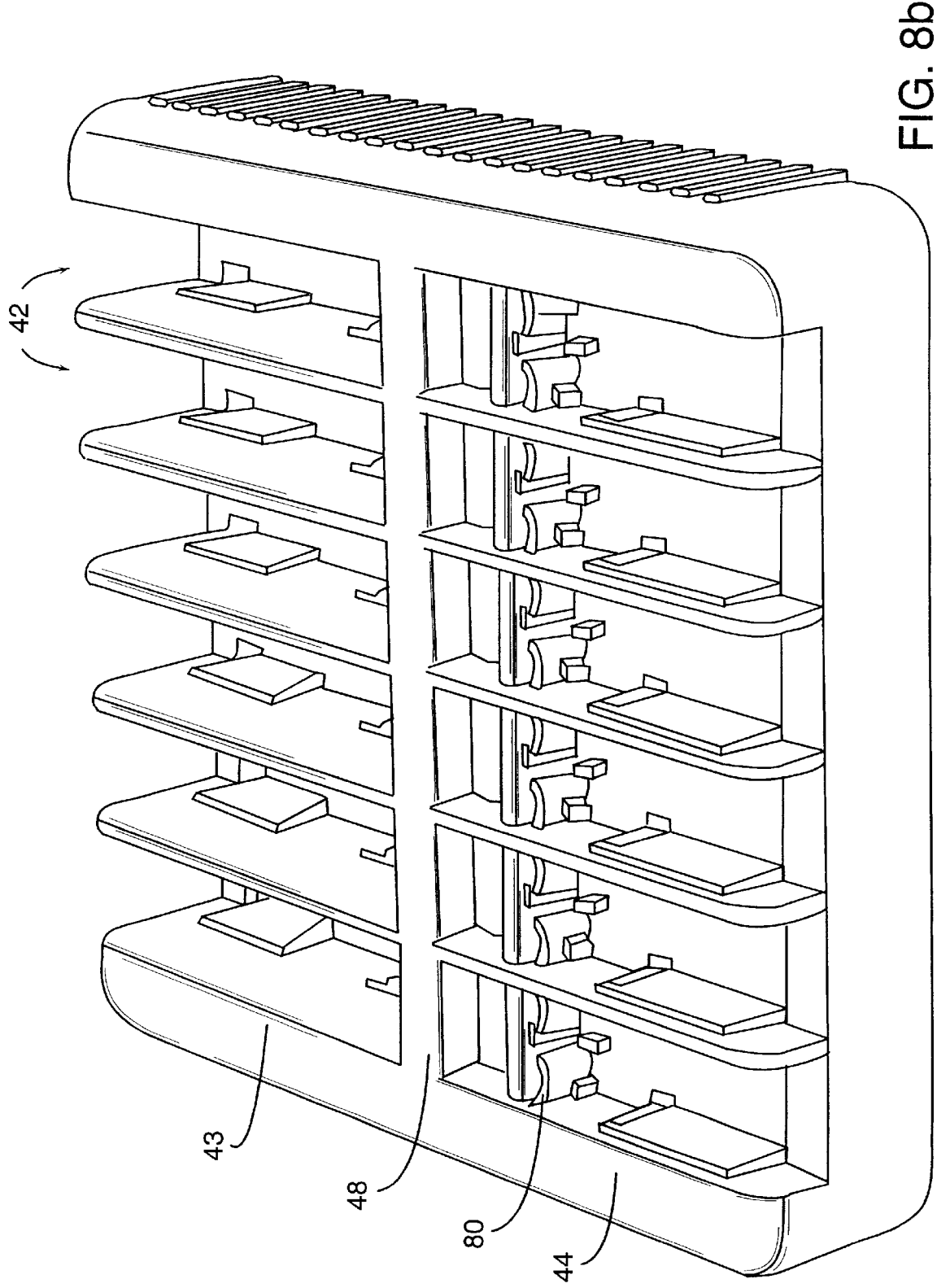
FIG. 8b shows a perspective view of a carrier cassette assembly in accordance with the present invention.

In the case where a cassette 40 is used, the carrier assemblies 30, each carrying a tack 1 are pre-mounted into the channels 42 of the pickup column 43, as shown in FIG. 8. The tack applicator 20 is simply pushed into a channel 42 as shown in FIG. 10, until the loading tip 24 engages and locks onto a carrier assembly 30. The tack applicator 20, with the mounted carrier assembly 30 bearing tack 1, is then withdrawn from the channel 42, FIG. 13.

The tack 1 is now ready for insertion into a desired site. The tack applicator 20 is positioned such that the sharp conical head 4 of the tack 1 is at the desired location for insertion. The user pushes the tack applicator 20 into the bodily tissue as the sharp conical head 4 of the tack 1 penetrates through the tissue. Once the desired depth had been reached, the user pulls the tack applicator 20 gradually out of the tissue. The tack's transverse locking member 8 and the proximal end 7 of the sharp conical head 4 resists backward motion out of the tissue, thereby disengaging the cannula's 34 hold on the tack 1 and leaving the tack 1 lodged within the tissue. The conical head 4 and the transverse locking member 8 hold the joined body tissue located between them.

Figure 14:
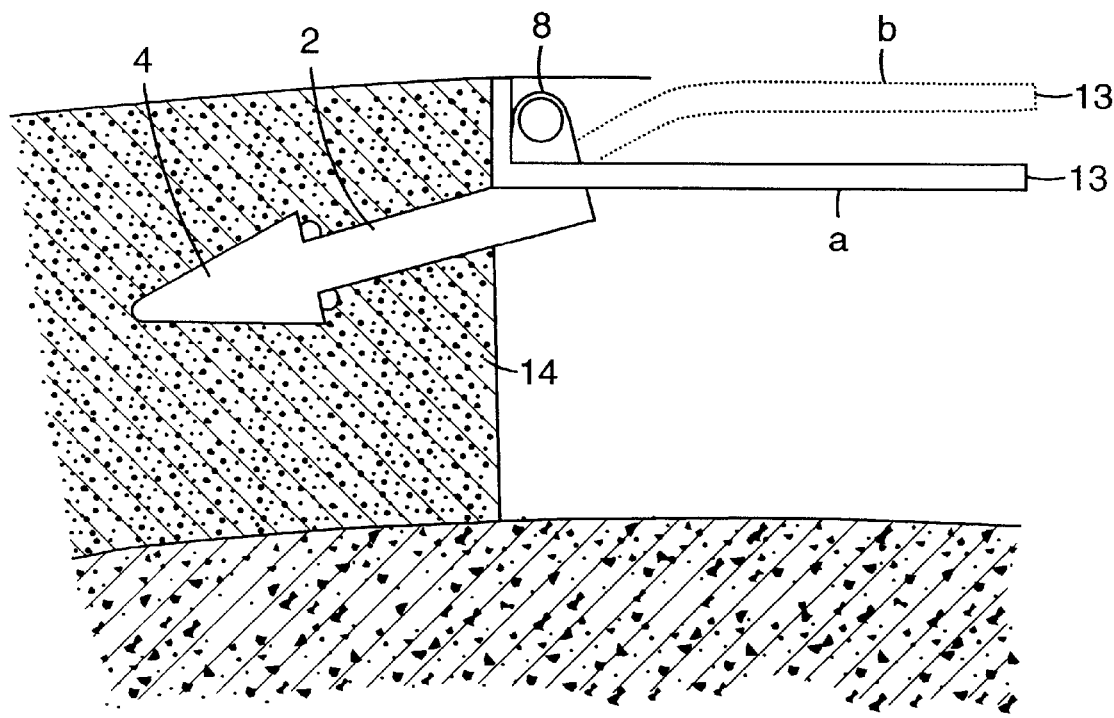
FIG. 14 shows the surgical tack of FIG. 1 being used repair cartilage by use of a natural or synthetic membrane patch.

The location of the transverse locking member 8 offset from the longitudinal axis 3 of the head 4 and the rod 2 further aids in the positioning and maintenance of the tack 1 in desired location. Specifically, for example, as shown in FIG. 14, in a procedure where a temporary patch 13, such as a periosteum patch is used to repair cartilage or bone by attaching the patch 13 over the cartilage or bone defect, the location of the transverse locking member 8 above the plane of the rod 2 ensures that the tack 1 can be buried deep into the underlying cartilage 14 while the temporary patch 13 is kept as close to flush with the articular surface 15 as possible. As shown in FIG. 14, the transverse locking member 8 is designed to impart a force vector on the tack 1 in a radial direction from the head 4 to the transverse locking member 8. This acts to pull the periosteum 13 upward under the transverse locking member 8, from position "a" to position "b", which ensures that the tack 1 can be burried deep within the cartilage or bone 14, and permits the tack 1 to form a seal between the two objects 13, 14 which is much cleaner and closer to flush with the surface of the joined objects.

If a cassette 42 is used, after insertion of the tack 1 into the site, the used carrier assembly 30 may be discarded in a used carrier assembly 30 disposal channel 44. The tack applicator 20 is pushed, loading tip 24 end first, into the channel 44. The channel 44 is designed to have means 80 of catching onto and gripping the used carrier assembly 30 and disengaging the carrier assembly 30 from the loading tip 24 as the tack applicator 20 is backed out of the channel 44. The tack applicator 20 is now ready for re-loading.

The tacks 1 and tack applicators 20 may be used in open procedures, and also in less invasive arthroscopic procedures. Depending on the particular type of procedure, the overall dimensions and shape of the tack applicator 20 and carrier assembly 30 vary.

Arthroscopic procedures are known, and generally involve the use of trocars, or other hollow delivery mechanisms, through which the various tools required during the procedure are inserted into the site. These trocars and other hollow delivery mechanisms are typically narrow elongate tubes that may be straight or curved, relatively flexible or rigid. The hollow delivery mechanisms are inserted through a small incision made near the site.

For example, shown in FIGS. 16–20, is one method of arthroscopically repairing cartilage in the knee using the surgical tacks 1 and applicators 20 in accordance with the present invention. The method generally comprises accessing and preparing the site, followed by fixation of a natural or synthetic membrane patch, such as a periosteal patch, over the cartilage defect.

Figure 15:
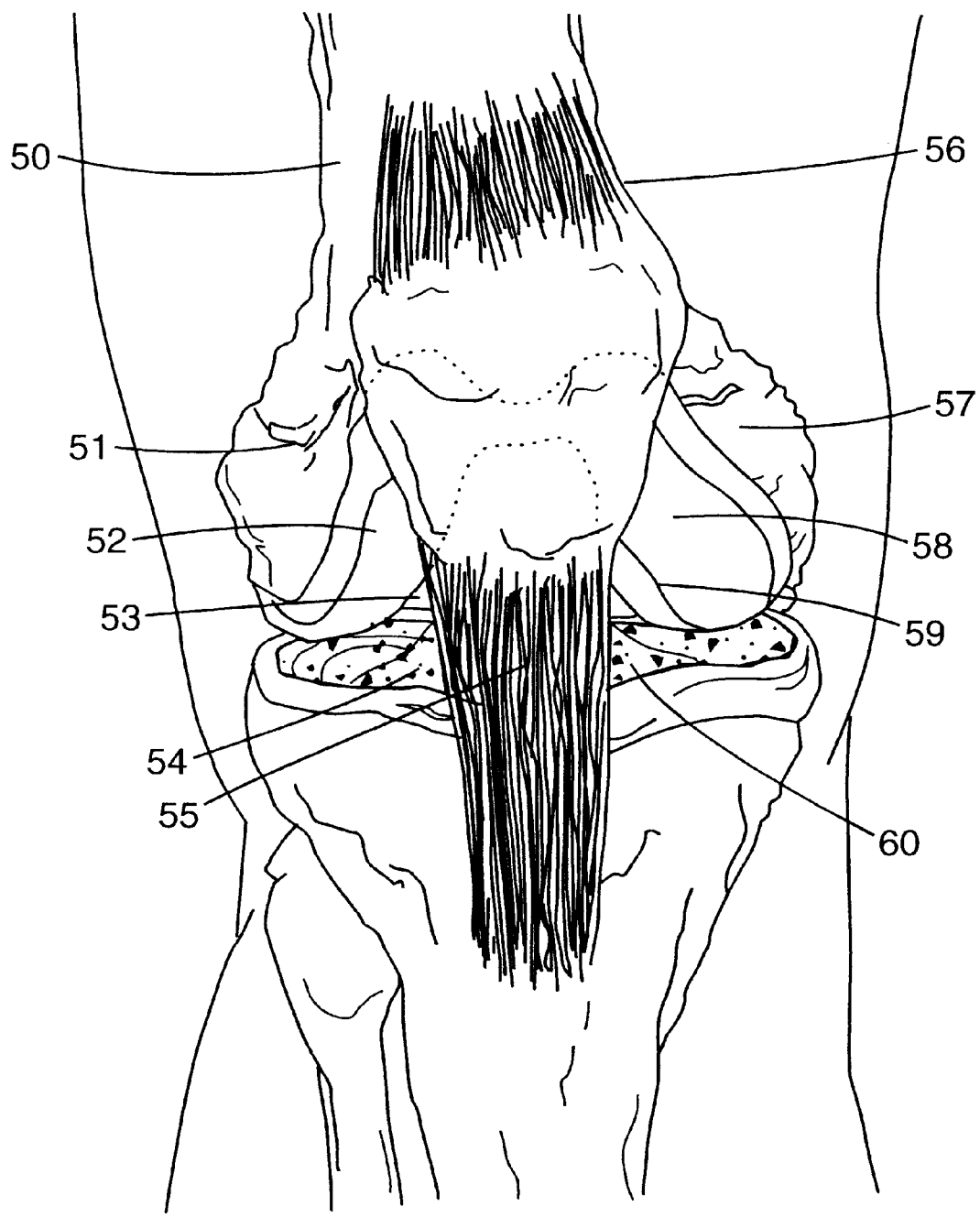
FIG. 15 shows a view of the portal sites to the right knee.

In arthroscopic procedures involving the right knee, the defect is accessed through any of the portal sights of the knee, shown in FIG. 15, which include the superolateral portal 50, lateral midpatellar portal 51, anterolateral portal 52, lateral auxillary portal 53, lateral parapatellar tendon portal 54, central transpatellar tendon portal 55, superomedial portal 56, medial midpatellar portal 57, anteromedial portal 58, medial auxiliary portal 59, and the medial parapatellar tendon portal 60. Similar portals and procedures may be used on the left knee.

Figure 16:
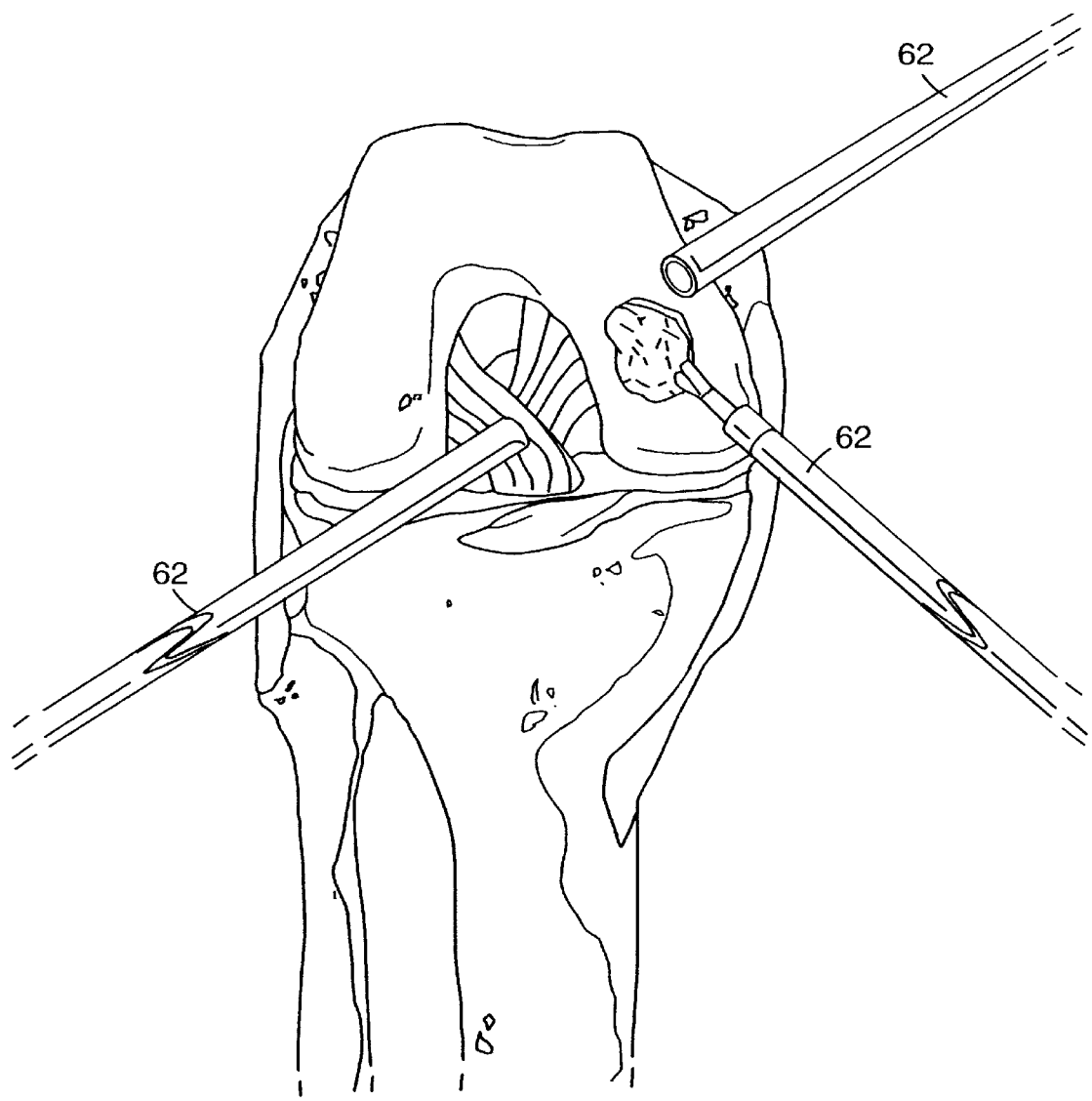
FIG. 16 shows one type of arrangement of trocars or hollow delivery tubes for use in arthroscopic procedures on the right knee.

A number of trocars or other hollow delivery mechanisms 62 may then be positioned for access to different areas of the knee. For example, FIG. 16 shows one possible portal usage combination for repairing a medial defect. In this combination, three portal sites are used in combination: (1) the central transpatellar tendon portal 55 may be used for insertion of a first hollow delivery mechanism 62, (2) the superomedial portal 56 may be used for insertion of a second hollow delivery mechanism 62, and (3) the anteromedial portal 58 or the medial auxiliary portal 59 may be used for inserting a third hollow delivery mechanism 62.

After accessing the site, the synovium is cleared away. The defect is then evaluated by conventional methods, such as probing it with a nerve hook and by gouging to determine the cartilage thickness. Next, the defect is circumscribed by conventional techniques. The cartilage is then debrided using any of the conventional tools to clean up the edges of the cartilage to form clean, perpendicular sidewalls. The defect is then measured for patch sizing. A template is next created using one of the alternatives available, such as simple measurement, pressure sensitive films and a 3-D digitizers. Blood from the site is cleared out and additional bleeding is stopped by sealing any bleeders. All of the above steps are carried out arthroscopically by inserting the appropriate tools through the hollow delivery mechanisms 62.

Figure 17:
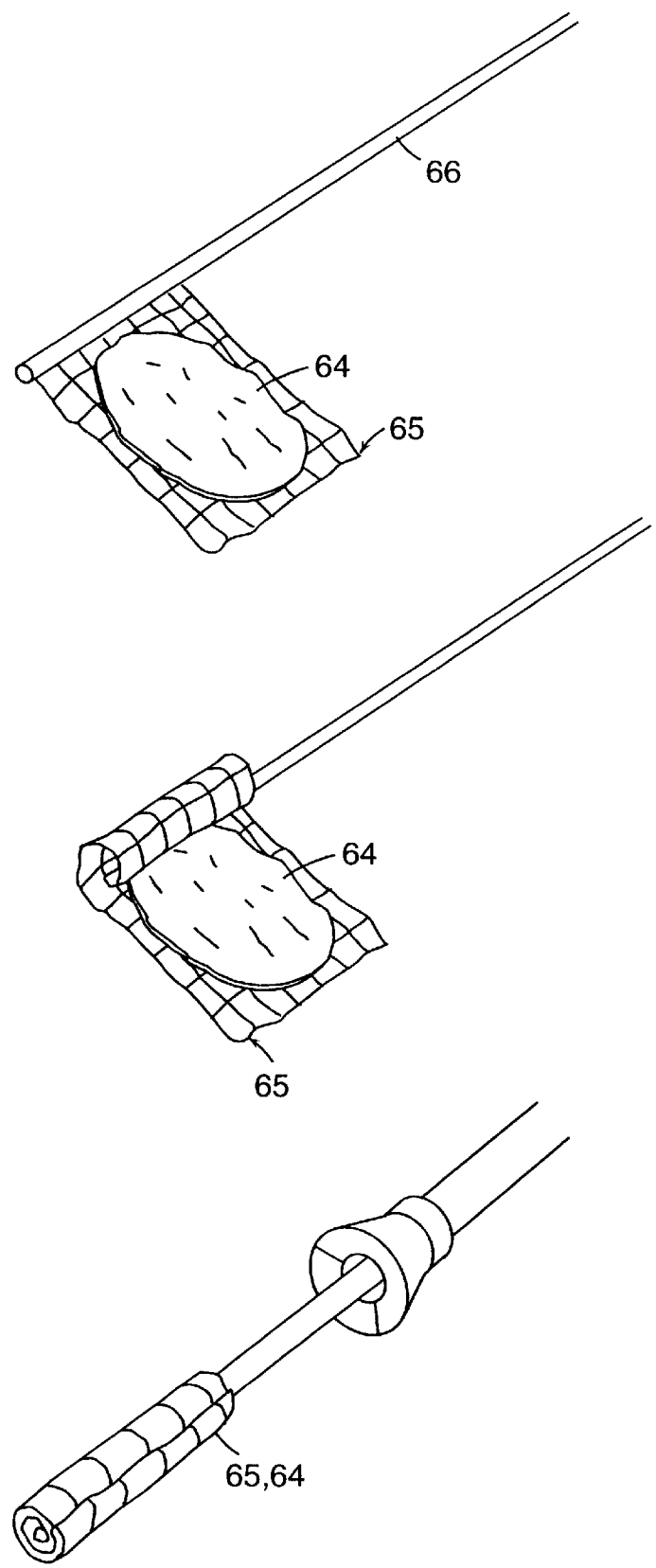
FIG. 17 shows one method of preparing a natural or synthetic membrane patch for arthroscopic insertion.
Figure 18:
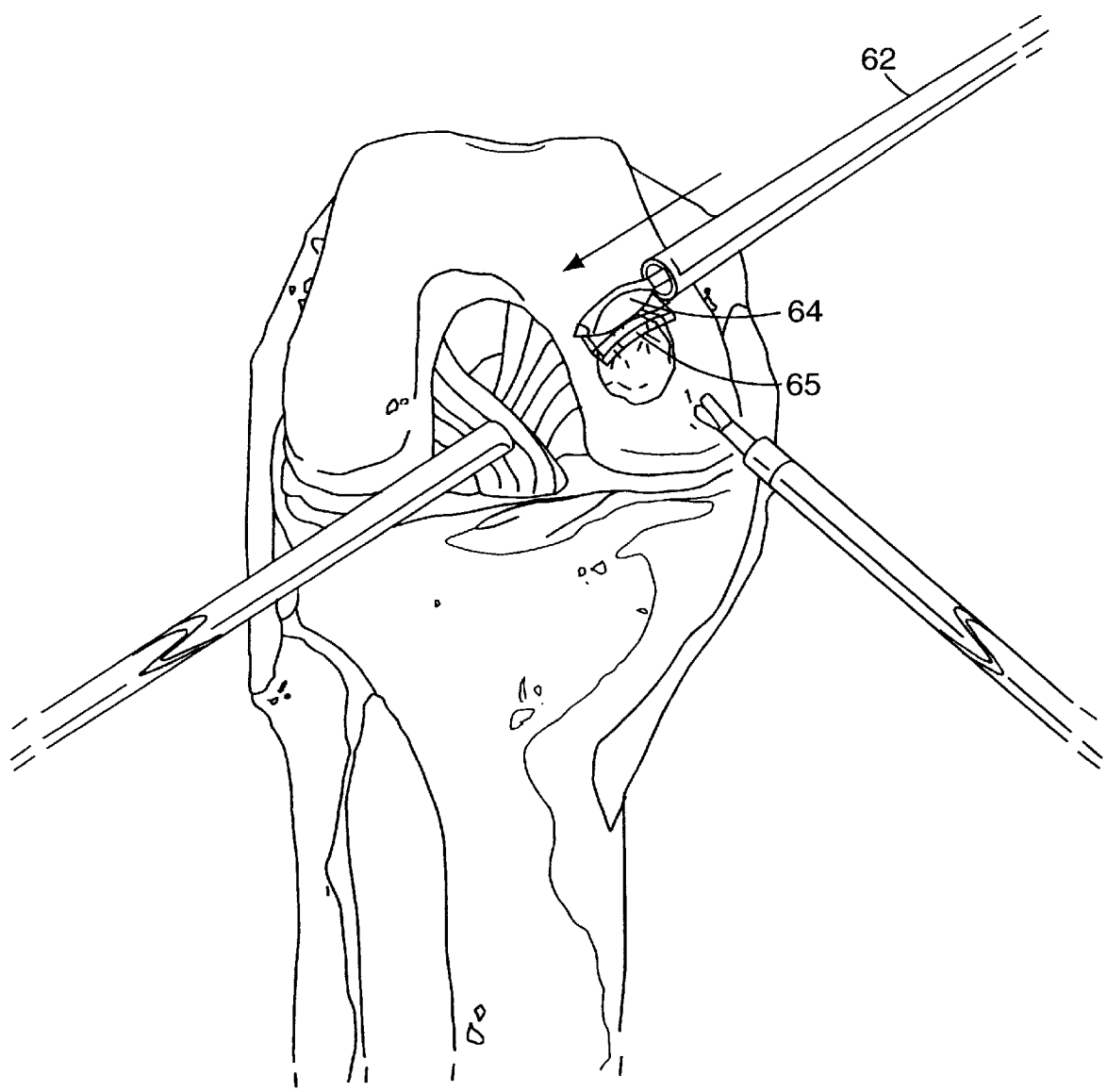
FIG. 18 shows the natural or synthetic membrane patch as prepared by FIG. 18 being inserted arthroscopically.
Figure 19:
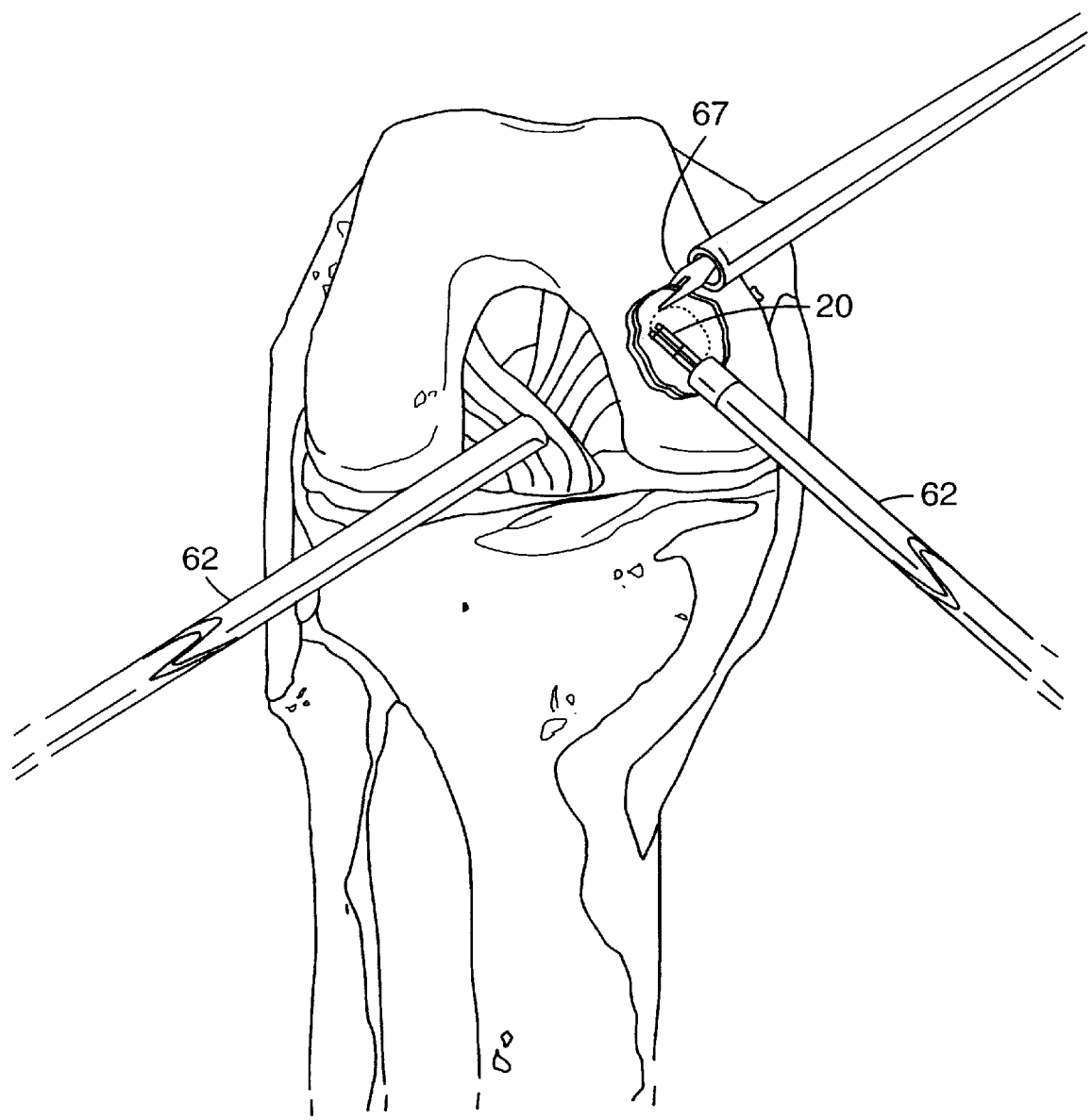
FIG. 19 shows a natural or synthetic membrane patch being fixed to a site arthroscopically.

Once the bleeding has been stopped, the patch may be transported by any conventional method, such as pulling the patch through one of the delivery mechanisms 62. Alternatively, the patch may be transported to the site by an alternate technique, such as transporting the patch in a rolled mesh carrier. As shown in FIG. 17, the patch 64 is first placed in the center of a mesh carrier backing 65 with the cambium side up. The carrier and patch are then rolled to form tight wraps by using, for example, a mandrel 66. The rolled mesh 65 and patch 64 may then be inserted into the delivery tube 62 and transferred to the site, where the mesh and patch are unrolled and the patch is positioned over the defect, as shown in FIG. 18. The patch may then be fixed to the site using the tacks 1 and applicators 20 of the present invention, as shown in FIG. 19.

If the Autologous Chondrocyte Implantation (ACI) technique is used, prior to fixing the patch to the site, the following is carried out: a biopsy tool is inserted through one of the hollow delivery mechanisms 62 to remove a biopsy of healthy cartilage tissue. The tissue is then cultured externally. After the site is prepared by the above procedure, the patch is fixed to cover the lesion by the above-described procedure. The cultured chondrocytes are then delivered into the lesion beneath the patch. Within the lesion, the cultivated cells produce matrix which integrates with the surrounding cartilage. Over time, the cells continue to mature and fill in the lesion with healthy cartilage.

While the overall design of the tacks and the tack applicators is generally the same for both the open and arthroscopic procedures, due to the nature of arthroscopic procedures, a narrower and longer applicator assembly is generally required for insertion through the hollow delivery mechanism.

For example, an extended carrier assembly 30 may be used. This mechanism may consist of a similar slotted 36 cannula 34 that is straight or curved. The cannula 34 may be mounted in a longer and more narrow carrier assembly 30 than the carrier assemblies used in open procedures.

As shown in FIG. 21, the carrier 30 may further have a cross section that is essentially rectangular, oval shaped, round with a notch or raised area or any other shape which helps maintain proper orientation of the tack 1. In some applications, as also shown in FIG. 21, the carrier assembly 30 may further be made of flexible or kerfed material so that it can be delivered through a curved trocar or other hollow delivery mechanism 62 with a similarly shaped cross section. This delivery mechanism 62 may be curved at the distal end to allow for improved access to some joint areas.

The tack applicator 20 and carrier assembly 30 may also allow for rotation of the delivery mechanism 62 to further improve joint access while still tracking the orientation of the tack 1. This type of assembly would allow replacement of carrier assemblies 30 with tacks 1 without losing location (triangulation) within the joint. It is also possible to utilize a carrier assembly 30 without a trocar 62 based on medical discretion.

Once the site is prepared and the patch is ready for fixation, the tack 1 is loaded into the cannula 34 of the carrier assembly 30 and the carrier assembly 30 is mounted into the loading tip 24 of the tack applicator 20 as described above.

The tack 1 is now ready for insertion into a desired site. The tack applicator 20 is inserted through one of the portals, such as the anteromedial portal 58 or the medial auxiliary portal 59, and positioned such that the sharp conical head 4 of the tack 1 is at the desired location for insertion into the patch 64. At the same time, as shown in FIG. 19, the patch 64 may be held by a grasping device 67. It is preferred that a plurality of tacks 1 are inserted along the periphery of the patch, close to the edges of the patch 64. A camera or viewing device may be inserted through tube 62 to provide the user with an enhanced view of the sight for proper tack 1 placement.

The tacks 1 of the present invention are designed to penetrate the patch 64 leaving only a small hole, which will diminish the likelihood of tearing through the edges of the patch 64. The conical head 4 of the tack 1 penetrates through the patch 64 and into the underlying cartilage. The tack 1 is preferably inserted such that the head 4 of the tack 1 does not penetratre through the cartilage, but rather remains burried within the cartilage, as shown in FIG. 14. Once the desired depth had been reached, the user pulls the tack applicator 20 gradually out of the portal. The tack's transverse locking member 8 and the proximal end 7 of the sharp conical head 4 resists backward motion out of the cartilage and patch, thereby disengaging the cannula's 34 hold on the tack 1 and leaving the tack 1 lodged within the cartilage. The conical head 4 and the transverse locking member 8 hold the tack 1 securely within the cartilage and patch 64 flush against the cartilage.

The preferably rounded edges of the transverse locking member 8 provides a gentle engagement with the delicate patch that resists tearing of the patch 64. The location of the transverse locking member 8 offset from the longitudinal axis 3 of the head 4 and the rod 2 aids in the positioning and maintenance of the tack 1 in desired location. As described above, the location of the transverse locking member 8 above the plane of the shaft ensures that the tack 1 can be buried deep into the underlying cartilage while the patch 64 is kept as close to flush with the articular surface of the cartilage as possible, as shown in FIG. 14.

Figure 20:
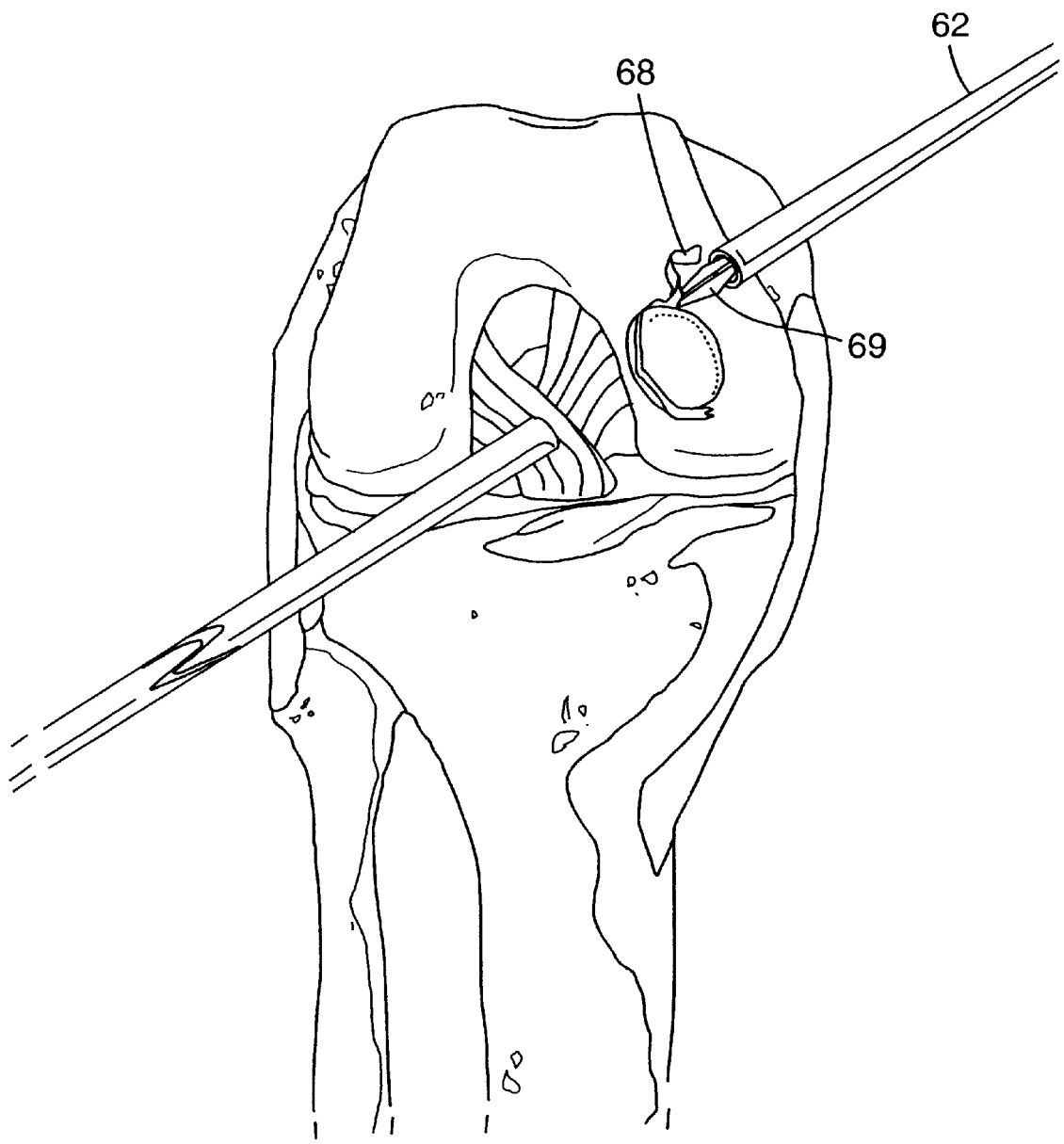
FIG. 20 shows excess patch being trimmed from the fixed patch arthroscopically.

The carrier assembly 30 may then be disposed of or discarded in a used carrier assembly 30 disposal channel 44 as described above, and the procedure is continued until the patch is fixed over the defect. After the tacks 1 are inserted about the patch 64 periphery, excess edges of the patch 68 may be trimmed flush to the edge of the defect using, for example, angles scissors 69 inserted through tube 62, as shown in FIG. 20.

What is claimed is:

1. A surgical fastener comprising:

an elongate rod having a front end portion and a back end portion;

a conical head at the front end portion of the rod;

a tail extending radially from a proximal portion of the rod; and a transverse locking member extending from the tail above and transverse to the longitudinal axis of the rod.

2. The surgical fastener of claim 1 wherein the conical head has a sharp distal end.

3. The surgical fastener of claim 1 wherein the conical head has a proximal end having a maximum diameter larger than the diameter of the elongate rod.

4. The surgical fastener of claim 3 wherein the proximal end of the conical head is substantially normal to the elongate rod.

5. The surgical fastener of claim 4 wherein the proximal end of the conical head terminates in a surface which is at substantially a right angle to the axis of the elongate rod.

6. The surgical fastener of claim 1 further comprising a ramp-shaped support extending from the proximal end of the conical head to the rod.

7. The surgical fastener of claim 1 wherein the fastener is formed out of a bioabsorbable material.

8. The surgical fastener of claim 1 further comprising at least one small protrusion on the rod, for engaging with the surface of a cannula.

9. A surgical fastening assembly comprising:
an applicator comprising:
    an elongate handle having a front end and a back end;
    a loading tip at the front end of the elongate handle;
    a carrier assembly removably mounted in the loading tip;
a surgical fastener removably mounted in the carrier assembly comprising:
    an elongate rod having a front end portion and a back end portion;
    a sharp conical head at the front end portion of the rod extending beyond and in front of the carrier; and
    a tail extending proximally at the back end portion of the rod and wherein the tail extends from the carrier; and
a cassette for holding and disposing of new and used carrier assemblies.

10. A surgical fastening assembly comprising:
an applicator comprising:
    an elongate handle having a front end and a back end;
    a loading tip at the front end of the elongate handle;
    a carrier assembly removably mounted in the loading tip;
a surgical fastener removably mounted in the carrier assembly comprising:
    an elongate rod having a front end portion and a back end portion;
    a sharp conical head at the front end portion of the rod extending beyond and in front of the carrier; and
    a tail extending proximally at the back end portion of the rod; and
    a cassette for holding and disposing of new and used carrier assemblies and wherein the cassette comprises a plurality of parallel channels each adapted to hold a carrier assembly.

11. The surgical fastening assembly of claim 10 wherein the plurality of parallel channels is divided into two columns wherein one column holds new carrier assemblies with mounted surgical tacks and the other column holds and receives used carrier assemblies.

12. The surgical fastening assembly of claim 11 wherein the plurality of parallel channels are sized to fit a carrier assembly with the surgical fastener at one end and a space behind the carrier assembly for insertion of the tack applicator whereby the tack applicator is automatically aligned in the parallel channels for proper pick-up of a carrier assembly.

13. The surgical fastening assembly of claim 11 wherein the plurality of parallel channels has guides located along the channel edges to aid in proper alignment and insertion of the applicator within the channels.

14. The surgical fastening assembly of claim 13 whereby the applicator includes notches on its front end corresponding to the guides located along the channel edges thereby further aiding in proper alignment and insertion of the applicator within the channels.

15. The surgical fastening assembly of claim 9 wherein the loading tip is spring loaded.

\* \* \* \* \*